(12) United States Patent
Hoffman et al.

(10) Patent No.: US 7,815,865 B2
(45) Date of Patent: *Oct. 19, 2010

(54) LIQUID DISPENSING DEVICE

(75) Inventors: John Hoffman, Poway, CA (US); James A. Benjamin, San Diego, CA (US); Janet M. Newman, Melbourne (AU); John Andrew Moulds, Encinitas, CA (US); David W Jewell, San Diego, CA (US); John A. Adams, Escondido, CA (US); Thomas E. Vomdran, Oceanside, CA (US); Brian L. Ganz, Carlsbad, CA (US)

(73) Assignee: Rigaku Automation, Inc., Carlsbad, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 12/111,646

(22) Filed: Apr. 29, 2008

(65) Prior Publication Data

US 2009/0068066 A1    Mar. 12, 2009

Related U.S. Application Data

(63) Continuation-in-part of application No. 10/764,710, filed on Jan. 24, 2004, now Pat. No. 7,364,702.

(51) Int. Cl.
*B01L 3/02* (2006.01)

(52) U.S. Cl. .......... 422/100; 422/99; 422/101; 422/102; 222/181.1; 222/548; 436/180

(58) Field of Classification Search .......... 422/99–102; 222/181.1, 548; 436/180
See application file for complete search history.

(56) References Cited

U.S. PATENT DOCUMENTS 7,364,702 B2 *   4/2008   Hoffman et al. ............ 422/100

* cited by examiner

*Primary Examiner*—Jyoti Nagpaul
(74) *Attorney, Agent, or Firm*—John R. Ross; John R. Ross, III

(57) ABSTRACT

A liquid dispensing device. The liquid dispensing device has a tray for holding a liquid at a relatively constant level. A syringe is used for drawing fluid from the tray. A liquid container containing a liquid is positioned upside-down in the tray. Atmospheric pressure on the liquid in the tray and a vacuum inside the liquid container prevents liquid from draining from the container except when the liquid level in the tray drops to a level sufficient to allow air into the liquid container and to allow fluid to flow from the liquid container into the tray. The fluid flows from the liquid container into the tray until the level of liquid in the tray returns to the relatively constant level. The positioning of the syringe for drawing fluid is simplified in that the level of fluid in the tray is maintained at an approximately constant level despite withdrawal of quantities of fluid from the tray.

21 Claims, 27 Drawing Sheets

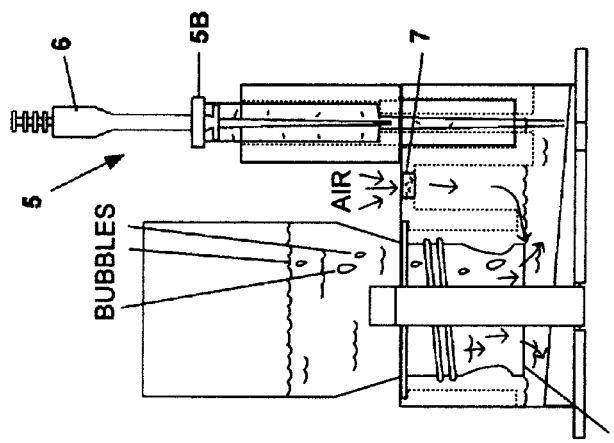

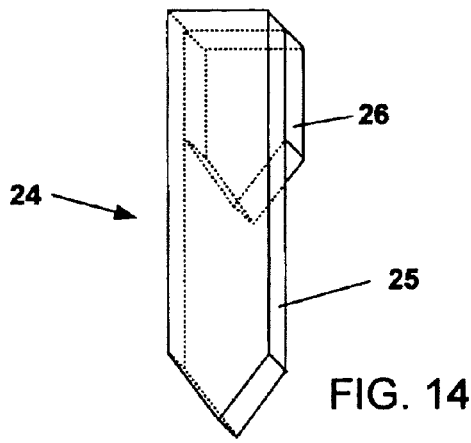
FIG. 14
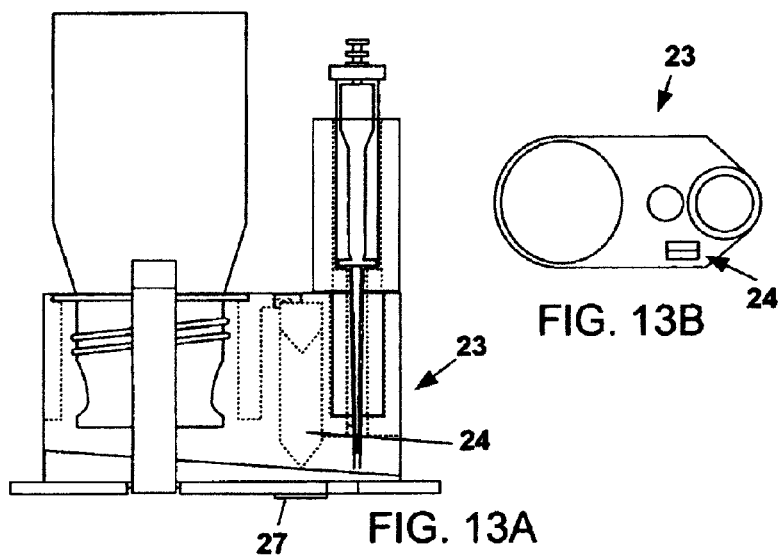
FIG. 13A
FIG. 13B
FIG. 13C
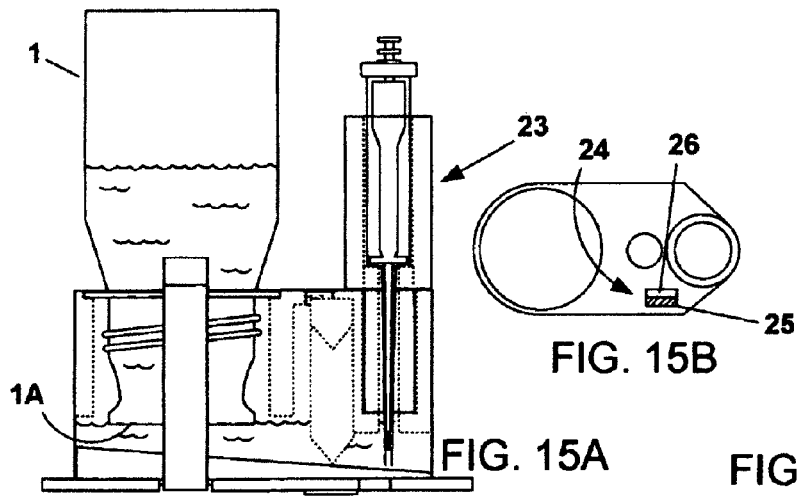
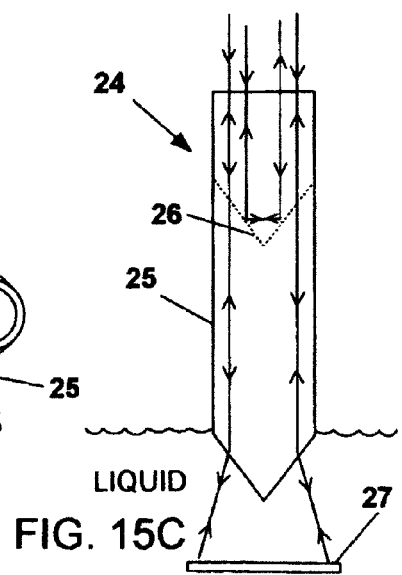
FIG. 15A
FIG. 15B
FIG. 15C

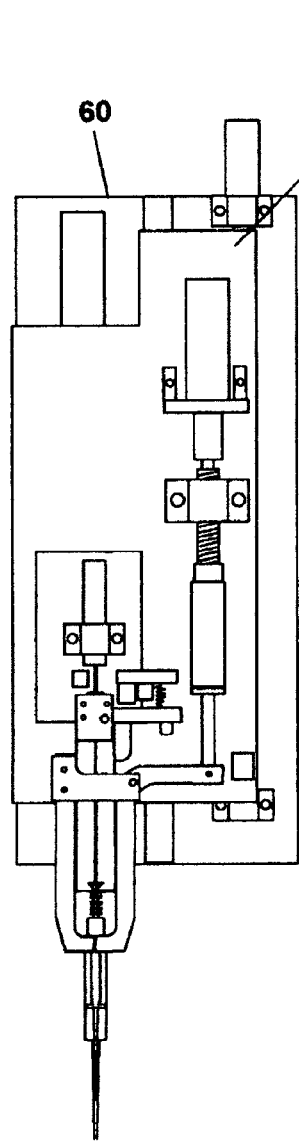 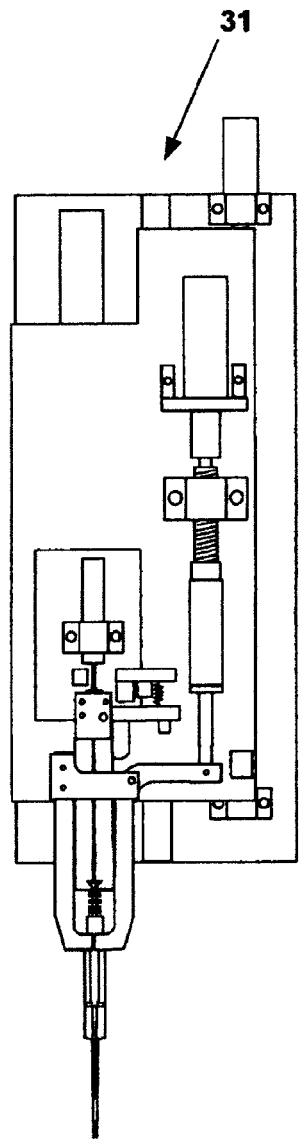 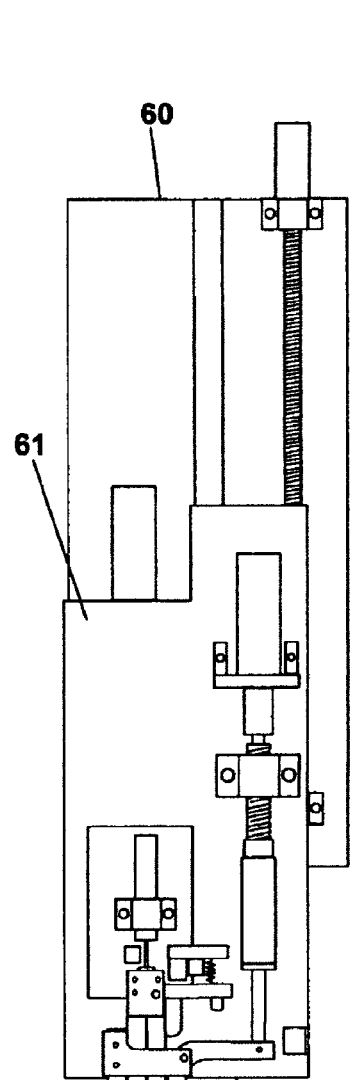
FIG. 36
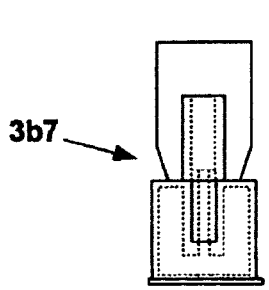
FIG. 37
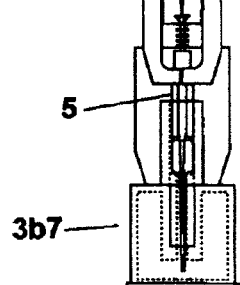
FIG. 38

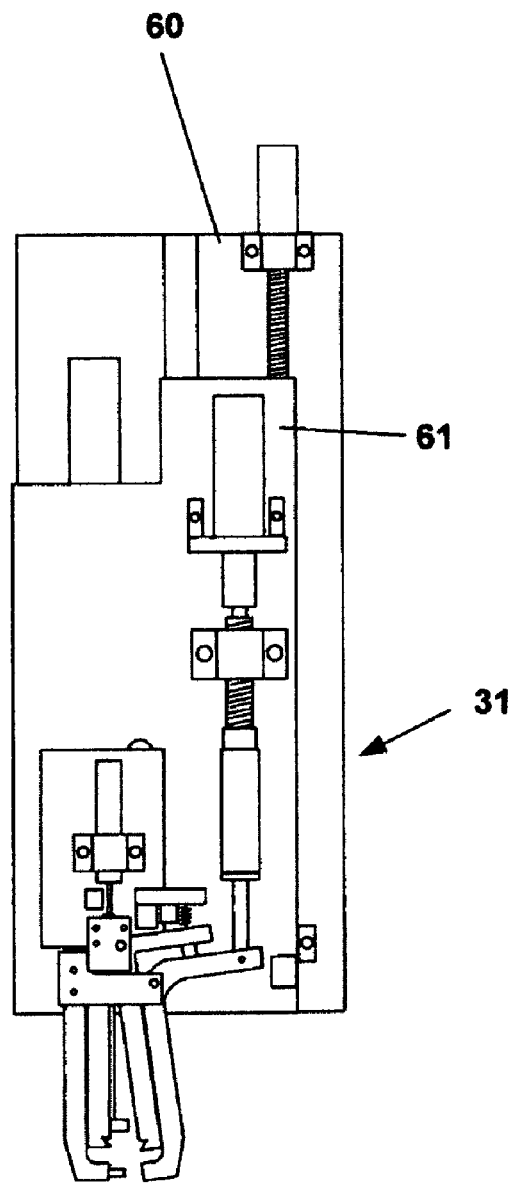
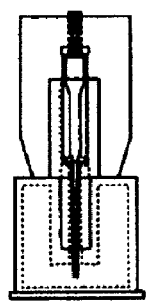
FIG. 42

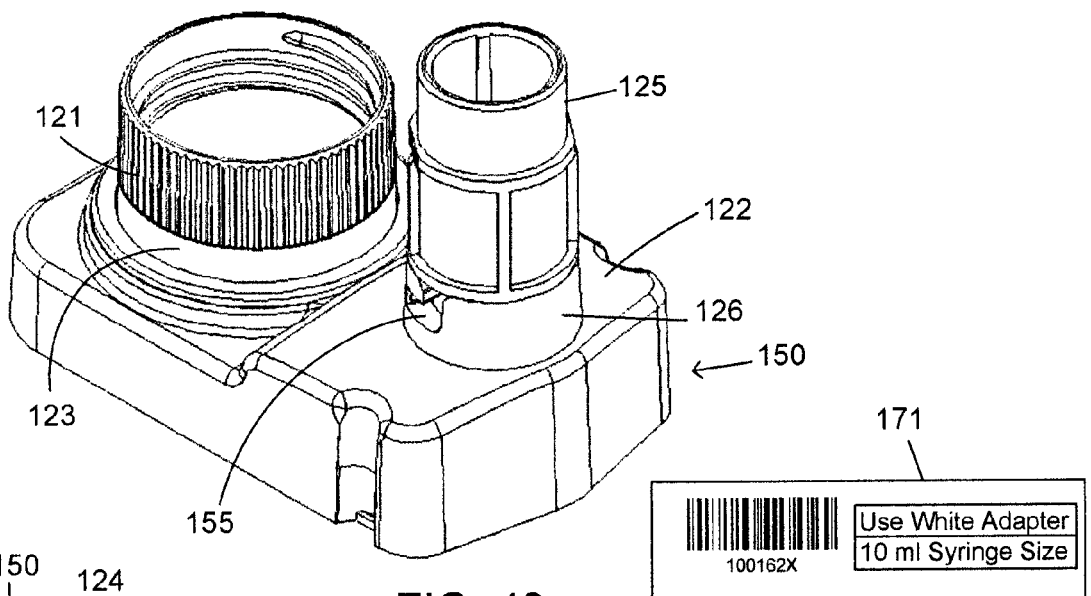
FIG. 48
```
Use White Adapter
10 ml Syringe Size
100162X
```
FIG. 49b
FIG. 50
FIG. 51
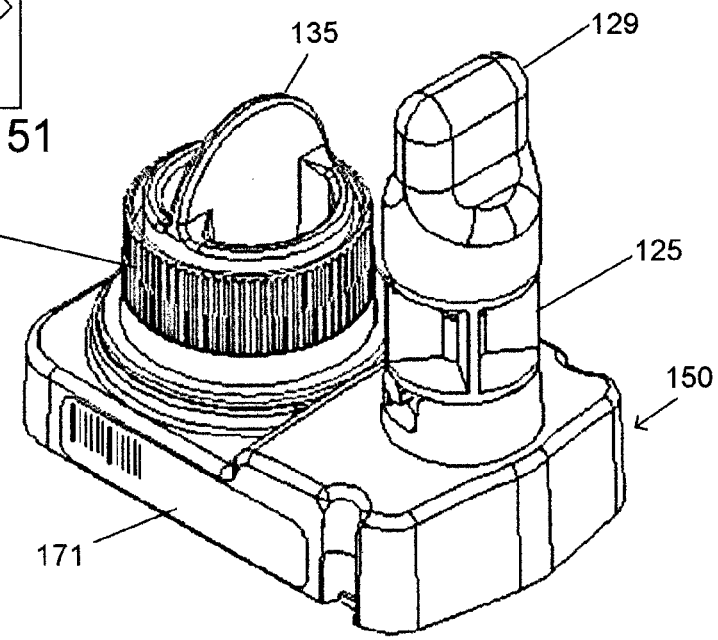
FIG. 49

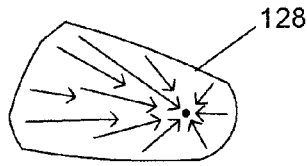
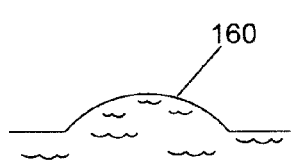
FIG. 54  FIG. 55  FIG. 56
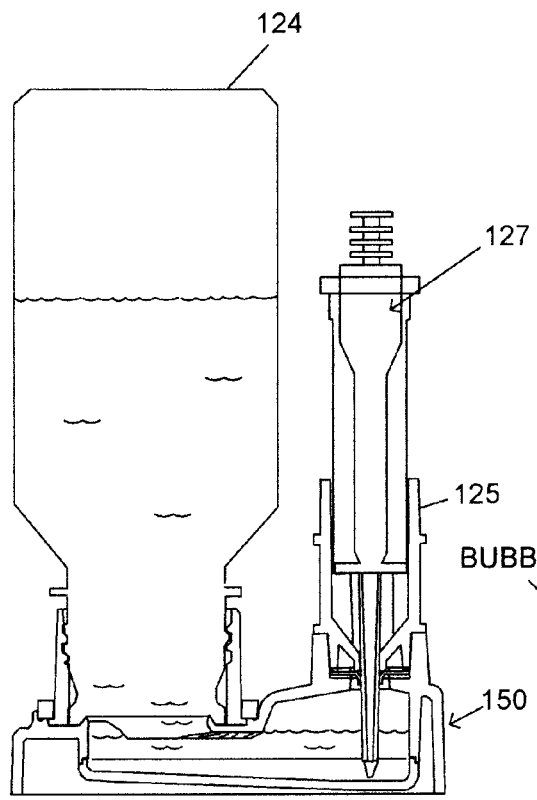
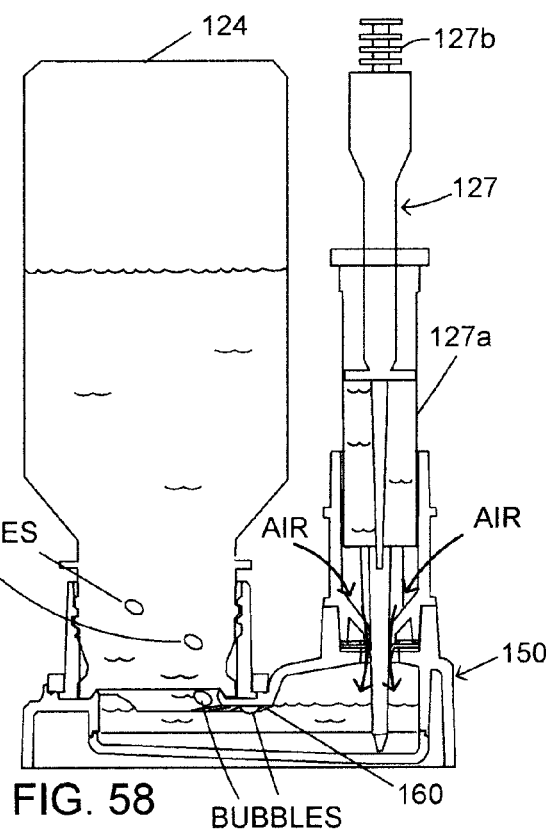
FIG. 57  FIG. 58
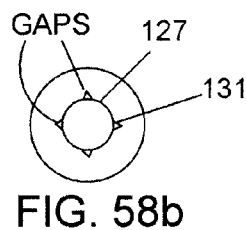
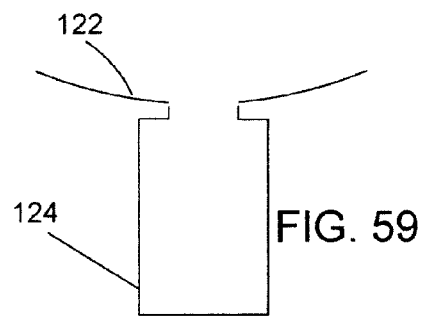
FIG. 58b  FIG. 59

LIQUID DISPENSING DEVICE

The present invention relates to liquid handling devices, and in particular, to liquid dispensing devices. The present application is a Continuation-in-Part application of U.S. patent application Ser. No. 10/764,710, filed Jan. 24, 2004; soon to issue as U.S. Pat. No. 7,364,702, which is incorporated by reference herein.

BACKGROUND OF THE INVENTION

Chemical solutions may be mixed either manually by a chemist or laboratory technician or they may be mixed automatically by an automated liquid mixing device. A syringe (also known as a pipette, pipettor or a micropipettor) may be used to transfer liquid from a bottle to a location where liquids are mixed, such as a micro-well plate.

For example, FIG. 1A shows prior art syringe 5 positioned over bottle 1B containing a liquid. In FIG. 1B, a technician has immersed the tip of syringe 5 into the liquid in bottle 1B. In FIG. 1C, the technician has pulled upward on plunger 6 with one hand while holding the bottom part of syringe 5 down with the other hand. Pulling upward on plunger 6 draws liquid into syringe 5. Syringe 5 can now be used for liquid dispensing.

There are problems with the prior art method of liquid dispensing illustrated in FIGS. 1A-1C. To draw liquid into the syringe it is only necessary to slightly immerse the tip of the syringe below the level of the liquid surface, as shown in FIG. 1D. However, a technician will typically over-immerse the syringe into the liquid. For example, as shown in FIG. 1C, the end of syringe 5 has been immersed far below the surface of the liquid in bottle 1B. As a result, after syringe 5 is removed from the liquid in bottle 1B, there will be an unnecessarily large amount of liquid adhered to the outside surface of syringe 5. This liquid can drip off, causing a mess and possibly causing contamination in the laboratory.

There are also similar problems with prior art automated liquid mixing devices. As with the manual method, prior art automated pipettors are ineffective at placing the syringe at the optimum level inside bottle 1B to prevent unnecessary liquid adhesion to the outside surface of syringe 5. The challenge for the prior art automated systems has been that as liquid is gradually removed from its bottle, the surface level of the liquid inside the bottle gradually decreases. Prior art systems have been unsuccessful in adjusting the degree to which the syringe is inserted into the bottle to appropriately account for the varying amount of liquid inside the bottle.

What is needed is a better liquid dispensing device.

SUMMARY OF THE INVENTION

The present invention provides a liquid dispensing device. The liquid dispensing device has a tray for holding a liquid at a relatively constant level. A syringe is used for drawing fluid from the tray. A liquid container containing a liquid is positioned upside-down in the tray. Atmospheric pressure on the liquid in the tray and a vacuum inside the liquid container prevents liquid from draining from the container except when the liquid level in the tray drops to a level sufficient to allow air into the liquid container and to allow fluid to flow from the liquid container into the tray. The fluid then flows from the liquid container into the tray until the level of liquid in the tray returns to the relatively constant level. The positioning of the syringe for drawing fluid is simplified in that the level of fluid in the tray is maintained at an approximately constant level despite withdrawal of quantities of fluid from the tray.

BRIEF DESCRIPTION OF THE DRAWINGS

FIGS. 5-12 show the operation of the first preferred embodiment of the present invention.

FIGS. 13A-16C show a second preferred embodiment of the present invention.

FIGS. 18-42 show the operation of the third preferred embodiment of the present invention.

FIG. 48 shows another perspective view of components of the fourth preferred embodiment.

FIG. 49 shows another perspective view of components of the fourth preferred embodiment.

FIG. 49b shows a preferred color coded bar code.

FIGS. 50 and 51 show a top view of the fourth preferred embodiment.

FIG. 54 shows a component of the fourth preferred embodiment.

FIGS. 55 and 56 show another component of the fourth preferred embodiment.

FIGS. 57 and 58 show the operation of the fourth preferred embodiment.

FIG. 58b shows another component of the fourth preferred embodiment.

FIG. 59 shows another component of the fourth preferred embodiment.

DETAILED DESCRIPTION OF THE PREFERRED EMBODIMENTS

Figures 10, 11:
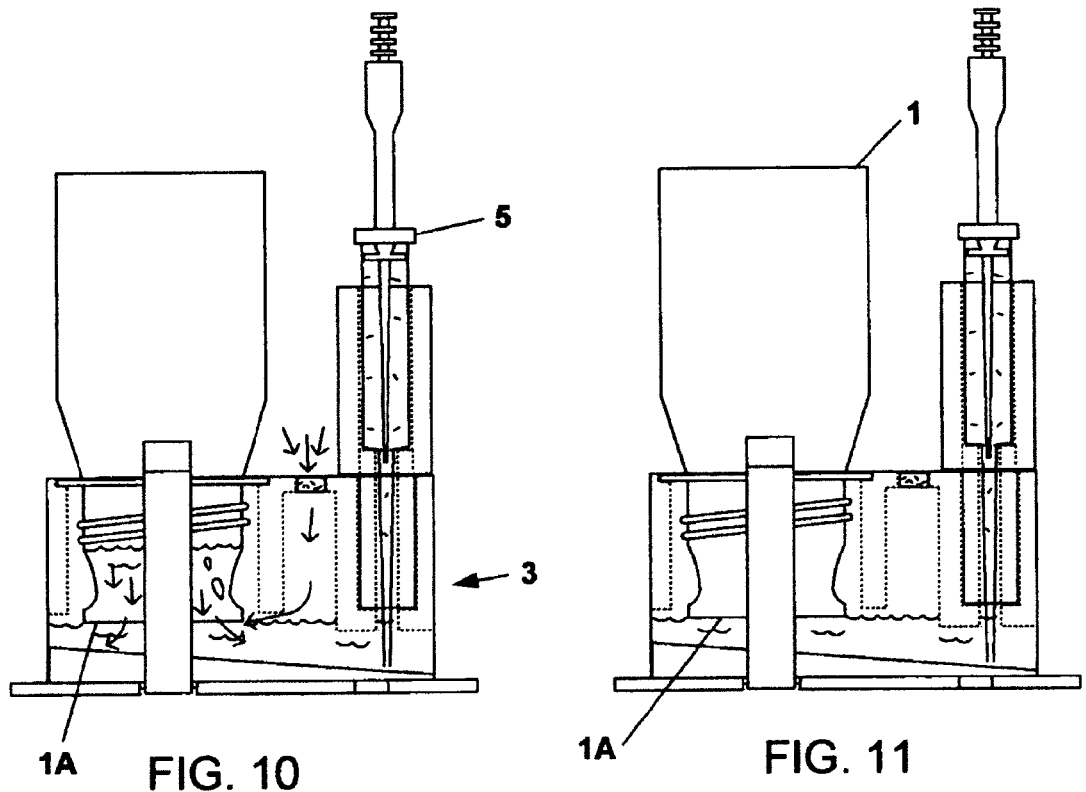

In a preferred embodiment of the present invention, tray 3 (FIG. 8) maintains an approximately constant dispensing level equal to or slightly above opening 1A of bottle 1 for syringe 5 as liquid is dispensed out of tray 3 (see FIGS. 9-11). By maintaining an approximately constant dispensing level, a laboratory technician or an automated dispensing device can more effectively and with less mess and error remove liquid from tray 3.

Manual Dispensing

First Preferred Embodiment

Liquid Dispenser

Figure 1A:
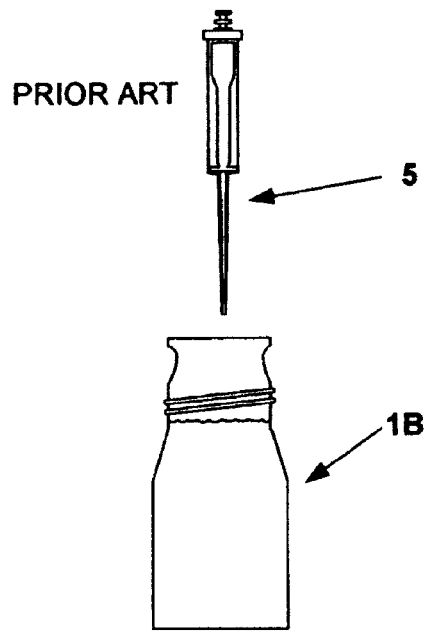
FIGS. 1A-1D show prior art methods for dispensing liquid from a bottle.
Figure 1B:
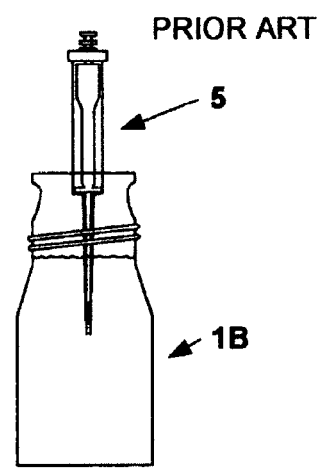
Figure 1C:
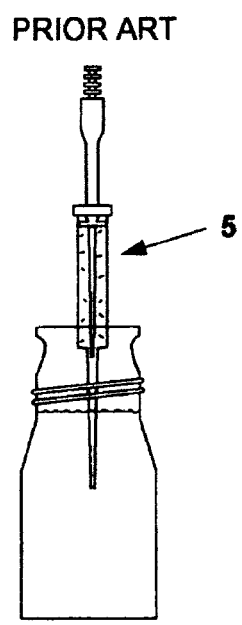
Figure 1D:
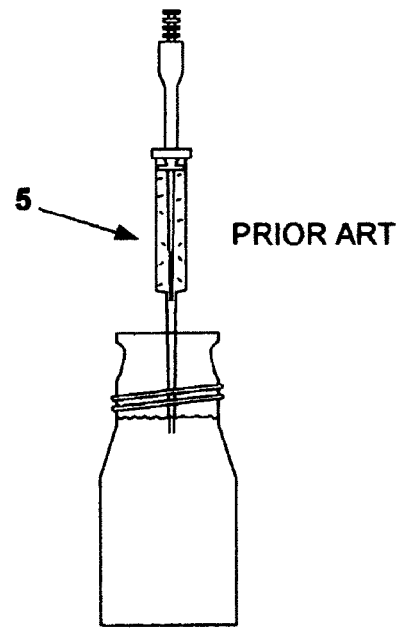
Figure 2A:
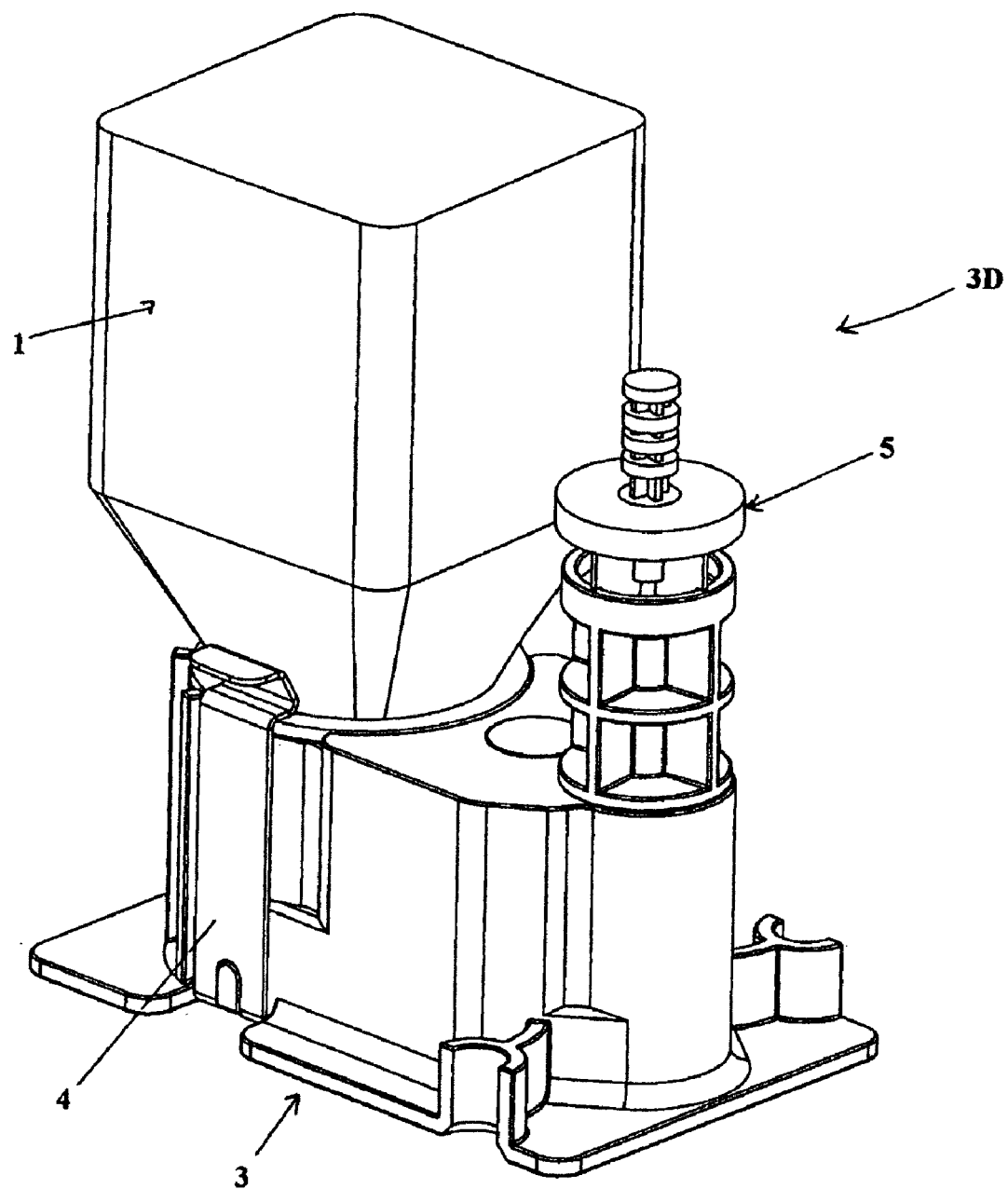
FIG. 2A shows a detailed perspective view of a first preferred embodiment of the present invention.
Figure 2B:
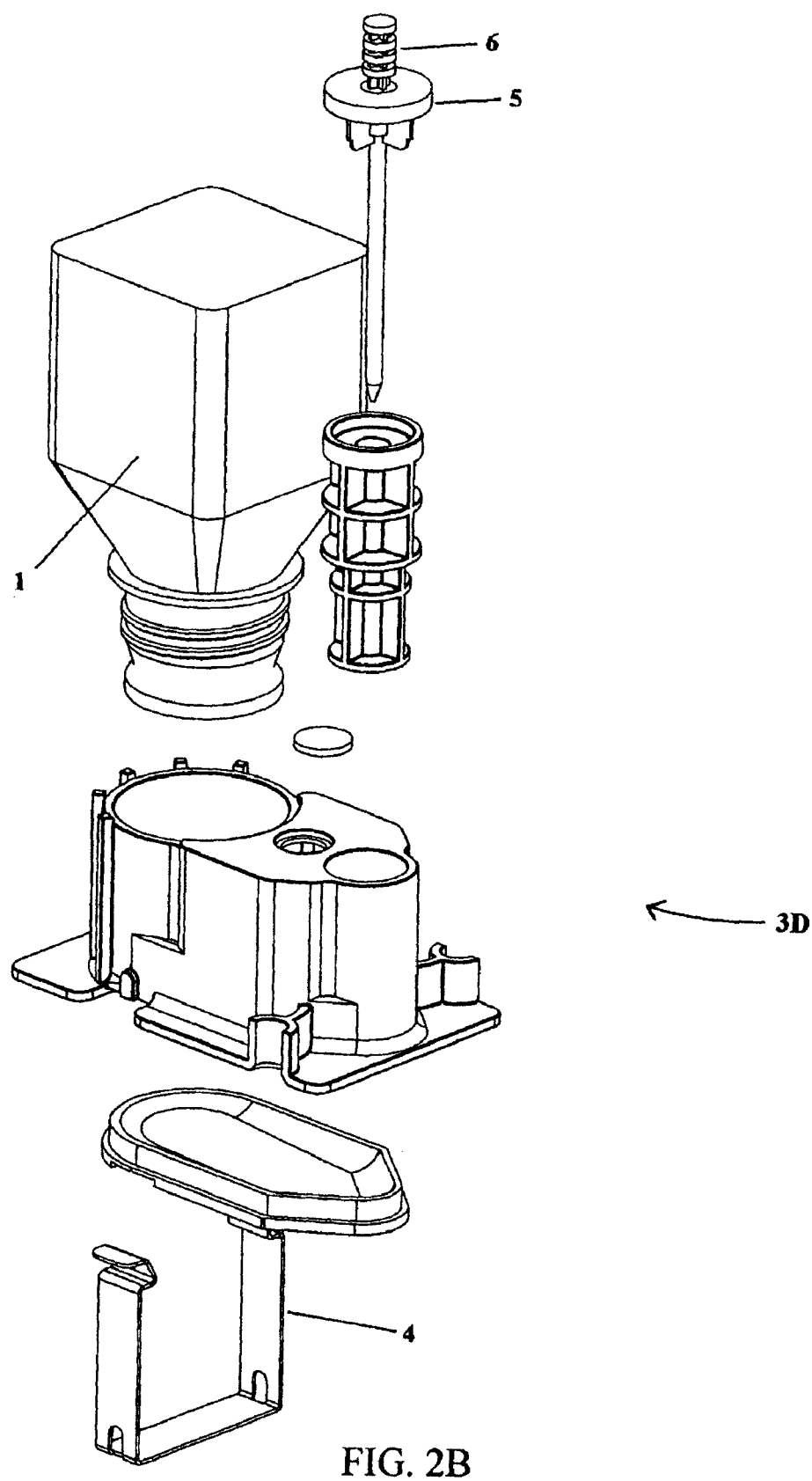
FIG. 2B shows a detailed exploded perspective view of a first preferred embodiment of the present invention.
Figure 3:
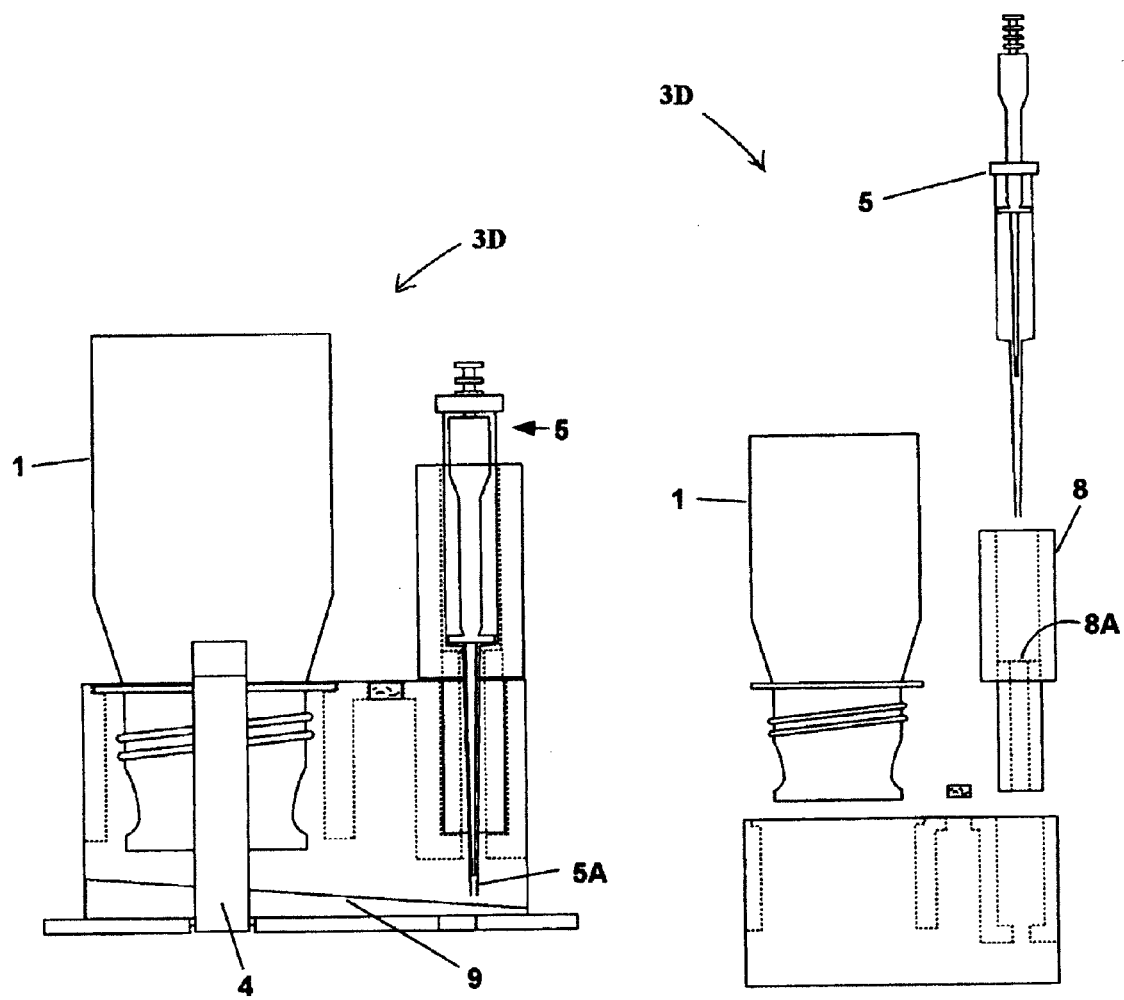
FIGS. 3 and 4 show a simplified front view and exploded view, respectively, of the first preferred embodiment.
Figure 4:
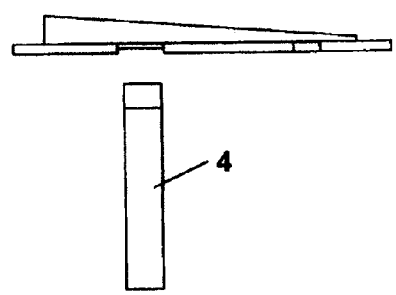

FIG. 2A shows a detailed perspective view and FIG. 2B shows a detailed exploded perspective view of liquid dispenser 3D. Likewise, FIGS. 3 and 4 show a simplified front view and exploded view, respectively, of liquid dispenser 3D.

In the first preferred embodiment, liquid to be dispensed is contained in upside-down bottle 1. As shown in FIG. 8, upside-down bottle 1 is held in place on top of tray 3 via metal bottle retaining clip 4. Preferably, tray 3 is fabricated from clear plastic. In the first preferred embodiment, a controlled amount of liquid flows out of bottle 1 and enters tray 3 where it is maintained inside tray 3 at an approximately constant level equal to or just slightly above the level of the level of the opening of bottle 1 as shown at 1A in FIG. 9. The liquid can then be easily removed by syringe 5 for further dispensing.

Operation of the First Preferred Embodiment

Prior to attaching bottle 1 to tray 3, bottle 1 is filled with liquid to be dispensed. FIG. 5 shows a side view of bottle 1 containing liquid.

In FIG. 6, tray 3 has been snap-fitted on top of bottle 1. Bottle 1 is preferably held in place via metal retaining clip 4 (also shown in more detail in FIG. 2A).

In FIG. 7, tray 3 and bottle 1 have been flipped over so bottle 1 is upside-down. A portion of the liquid that was in bottle 1 has flowed out of bottle 1 and into tray 3. The liquid will continue to flow out of bottle 1 until the level of liquid inside tray 3 is equal to or just slightly above the level of opening 1A of bottle 1. The combined effects of 1) atmospheric pressure exerting its force onto the surface of the liquid inside tray 3 and 2) the vacuum formed inside bottle 1 counter the effects of gravity and function to prevent the remainder of the liquid inside bottle 1 from emptying.

In FIG. 8, syringe 5 has been inserted into syringe holder 8 of tray 3. Syringe holder 8 includes abutment 8A (as shown in FIG. 4 and FIG. 7). Abutment 8A prevents further downward movement of syringe 5 and controls the location of tip 5A of syringe 5 so that tip 5A extends below the surface of the liquid inside tray 3 to a position just above the level of tilted bottom component 9 as shown in FIG. 8 (see also FIG. 3).

In FIG. 9, a user has grabbed syringe plunger 6 with one hand and has pulled it upward while holding syringe body 5B down with the other hand. The upward movement of syringe plunger 6 has caused liquid from tray 3 to be drawn up inside syringe 5. As liquid is drawn up inside syringe body 5B, the surface level of the liquid inside tray 3 decreases until eventually the level is below the level of opening 1A. Air is able to enter tray 3 via air filter 7. As the surface level decreases below the level of opening 1A, the vacuum inside bottle 1 will be momentarily broken as air is able to enter bottle 1 and flow upward as air bubbles through the liquid in bottle 1. As the air bubbles are flowing upward, liquid inside bottle 1 is filling tray 3. Liquid will continue to flow out of bottle 1 until once again the level of liquid inside tray 3 is equal to or slightly above the level of opening 1A of bottle 1, sealing off opening 1A and allowing the vacuum inside bottle 1 to reestablish.

In this fashion, liquid can be removed from tray 3 by syringe 5. After liquid has been removed from tray 3 via syringe 5, the user utilizes syringe 5 to deposit the removed liquid into a liquid receptacle device. For example in the first preferred embodiment, utilizing syringe 5, the user transfers liquid from tray 3 to a well in a micro-well plate.

While liquid is being removed, tray 3 maintains the level of the liquid inside tray 3 at a level equal to or just slightly above the level of opening 1A of bottle 1. For example, in FIG. 10 a user utilizing syringe 5 has removed a significant amount of liquid from tray 3 so that the level of liquid inside bottle 1 has decreased to level much lower than that shown in FIG. 9. However, the level inside tray 3 will rise until it is equal to or just slightly above the level of opening 1A. In FIG. 11, the user has removed even more of the liquid from tray 3 so that bottle 1 is approximately empty. The level of the liquid inside tray 3 is approximately equal to the level of opening 1A.

Figure 12:
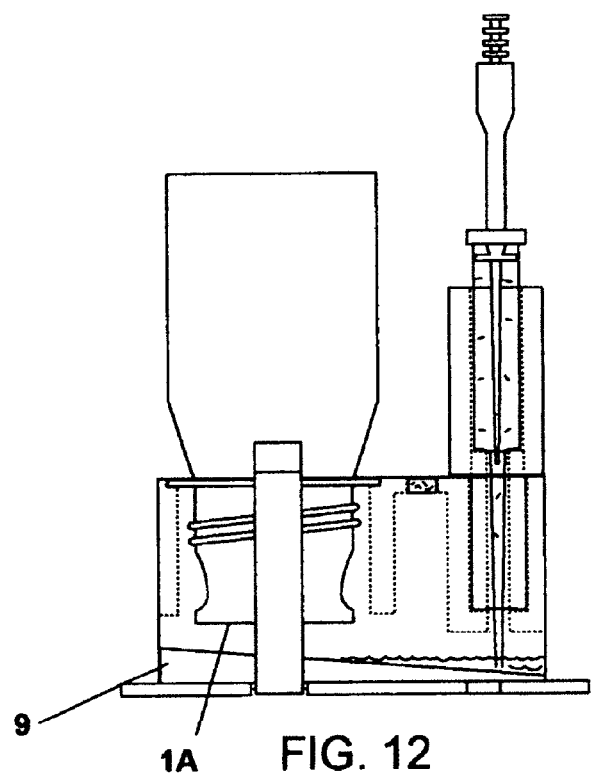

In FIG. 12, even more liquid has been removed from tray 3. After all the liquid has been removed from bottle 1, the user continues to remove liquid from tray 3, causing the level of the liquid to go below that of opening 1A. Tilted bottom component 9 has caused the remaining liquid inside tray 3 to puddle below the area of syringe 5 so that liquid can still be easily removed.

Second Preferred Embodiment

A second preferred embodiment is shown in FIGS. 13A and 13B. In the second preferred embodiment, tray 23 includes liquid level indicator 24. Below liquid level indicator is black tape strip 27. A detailed perspective view of liquid level indicator 24 is shown in FIG. 14. In the second preferred embodiment, liquid level indicator 24 is fabricated from clear plastic. Preferably, liquid level indicator 24 includes both low level indicator 25 and high level indicator 26.

Operation of the Second Preferred Embodiment

In FIG. 13A, liquid tray 23 is empty. This will cause light rays entering liquid level indicator 24 to be totally internally reflected as shown in FIG. 13C. Therefore, a user looking down onto the top of tray 23 will see that both low level indicator 25 and high level indicator 26 of liquid indicator 24 appear to be whitish, as shown in FIG. 13B.

In FIG. 15A, liquid tray 23 is filled so that the level of the liquid in tray 23 is slightly above the level of opening 1A. As explained above in reference to the first preferred embodiment, the preferred level of the liquid in tray 23 is equal to or just slightly above the level of opening 1A. In FIG. 15A, the pointed tip of low level indicator 25 is submerged in the liquid in tray 23 and the pointed tip of high level indicator 26 is above the liquid in tray 23. Because the pointed tip of low level indicator is submerged, light rays entering low level indicator 25 will be refracted as shown in FIG. 15C so that they will be partially absorbed and partially reflected by black tape strip 27. Conversely, because the pointed tip of high level indicator 26 is above the liquid in tray 3, light rays entering high level indicator 26 will be totally internally reflected. Therefore, a user looking down onto the top of tray 23 will see that low level indicator 25 appears to be black and that high level indicator 26 appears to be whitish, as shown in FIG. 15B.

Figure 16C:
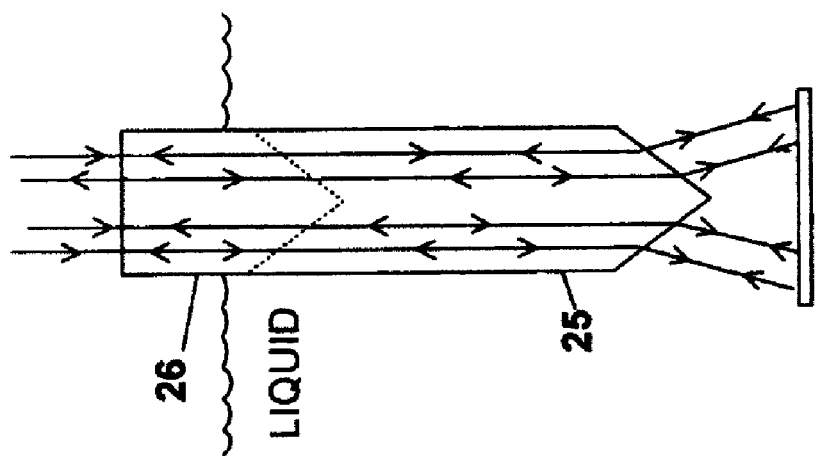
Figure 16B:
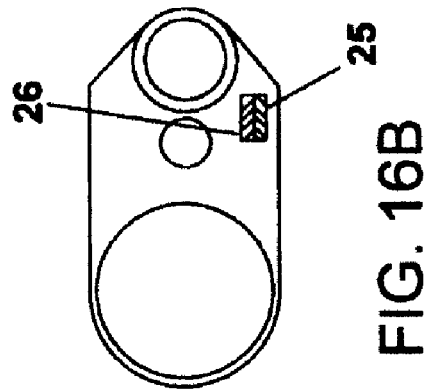
Figure 16A:
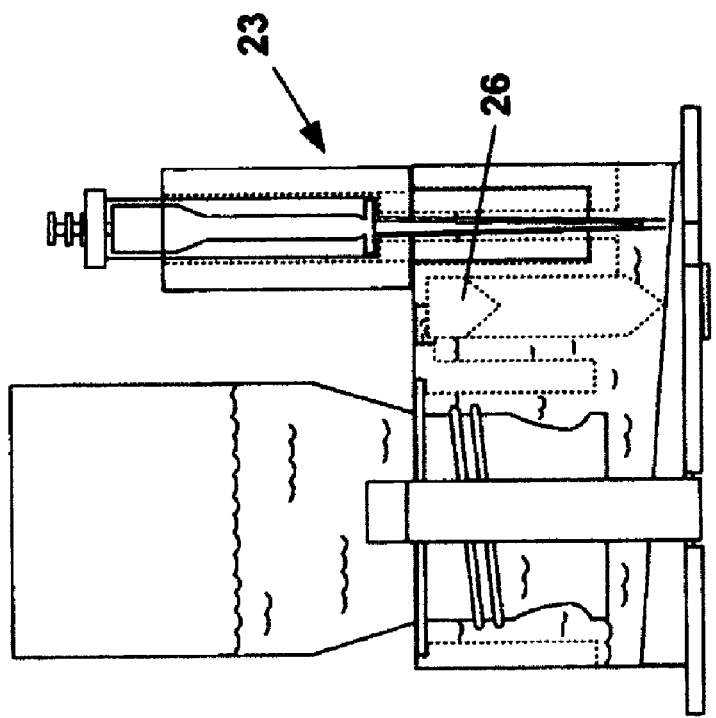

Although liquid tray 23 functions to keep the level of liquid inside tray 23 at a level equal to or just slightly above opening 1A as shown in FIG. 15A, the level inside tray 23 can rise to a higher level if, for example, tray 23 is inadvertently bumped or tilted breaking the vacuum inside bottle 1 and allowing air to enter bottle 1. In FIG. 16A, liquid tray 23 is filled so that the level of the liquid in tray 23 is above the level of high level indicator 26. The pointed tips of both low level indicator 25 and high level indicator 26 are submerged in the liquid in tray 23. Because the pointed tips of both level indicators are submerged, light rays entering level indicators 25 and 26 will be refracted as shown in FIG. 16C so that they will be partially absorbed and partially reflected by black tape strip 27. Therefore, a user looking down onto the top of tray 23 will see that low level indicator 25 and high level indicator 26 appear to be black, as shown in FIG. 16B.

Automated Liquid Handling Device

Third Preferred Embodiment

A third preferred embodiment is shown in FIGS. 17 to 42. In the third preferred embodiment an array of liquid dispensers similar to the dispensers described above are situated on platform 30 (FIG. 17). Computer 32 is programmed to automatically position robotic syringe grabber 31 over a selected liquid dispenser. Robotic syringe grabber 31 then automatically grabs syringe 5 from the selected liquid dispenser and draws liquid into the syringe in a fashion similar to that described above in reference to earlier preferred embodiments. Because the liquid dispensers situated on platform 30 maintain the level of the liquid to be dispensed at an approximately constant level. Syringe 5 is positioned so that its tip is submerged an optimum distance into the liquid to be dispensed. Therefore, robotic syringe grabber 31 does not have to be programmed to account for varying liquid levels. Robotic syringe grabber 31 then transfers the liquid to a liquid receiving device (such as micro-well plate 33A) where the liquid is dispensed.

Example of Operation of Third Preferred Embodiment

Figure 17:
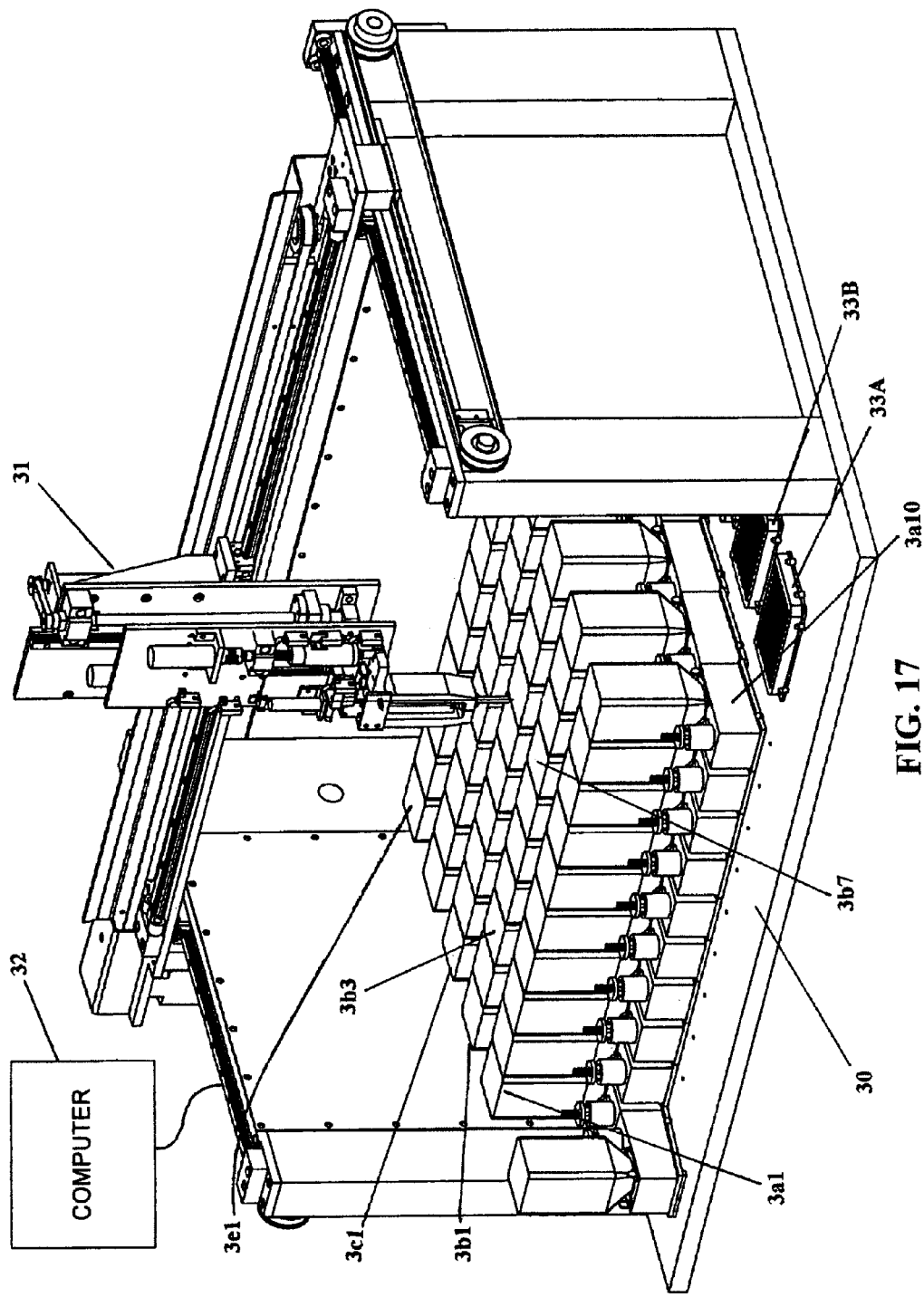
FIG. 17 shows a perspective view of a third preferred embodiment of the present invention.
Figure 18:
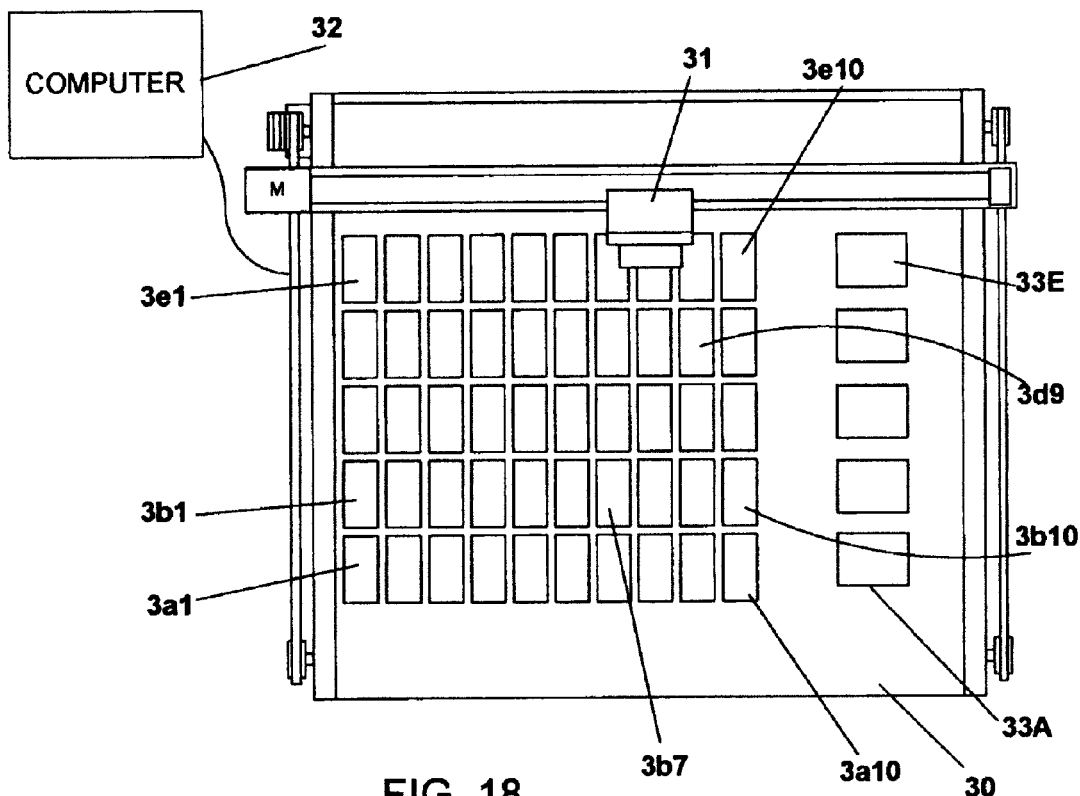
Figure 19:
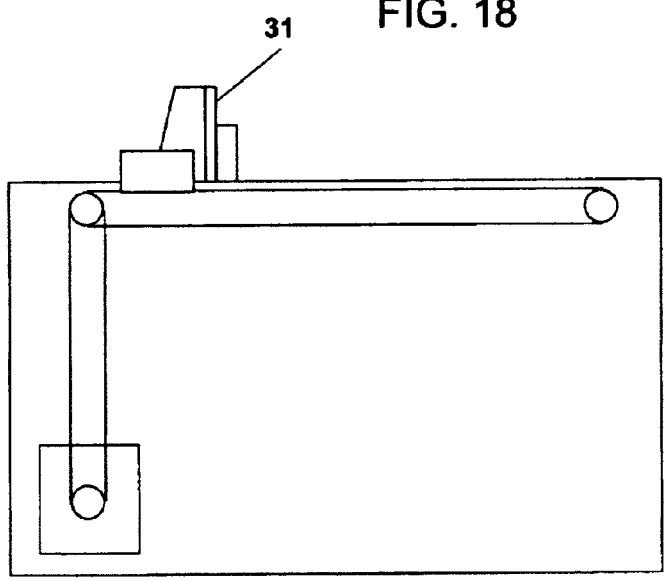

A detailed perspective view of the third preferred embodiment is shown in FIG. 17. A top view and left side view is shown in FIGS. 18 and 19, respectively. Dispensers 3a1-3e10 and micro-well plates 33a-33e are arranged on platform 30. Dispensers 3a1-3e10 are each similar to liquid dispenser 3D described above. Robotic syringe grabber 31 is controlled by computer 32. In the third preferred embodiment, computer 32 is programmed to control robotic syringe grabber 31 to draw liquid into syringes 5 of the selected dispensers. Robotic syringe grabber 31 is then controlled by computer 32 to remove syringes 5 from the selected dispensers and transfer the liquid in the syringe to pre-selected micro-well plates.

In the following example, computer 32 is programmed to control robotic syringe grabber 31 to remove syringe 5 located in dispenser 3b7 and transfer the liquid to micro-well plate 33a.

Figure 20:
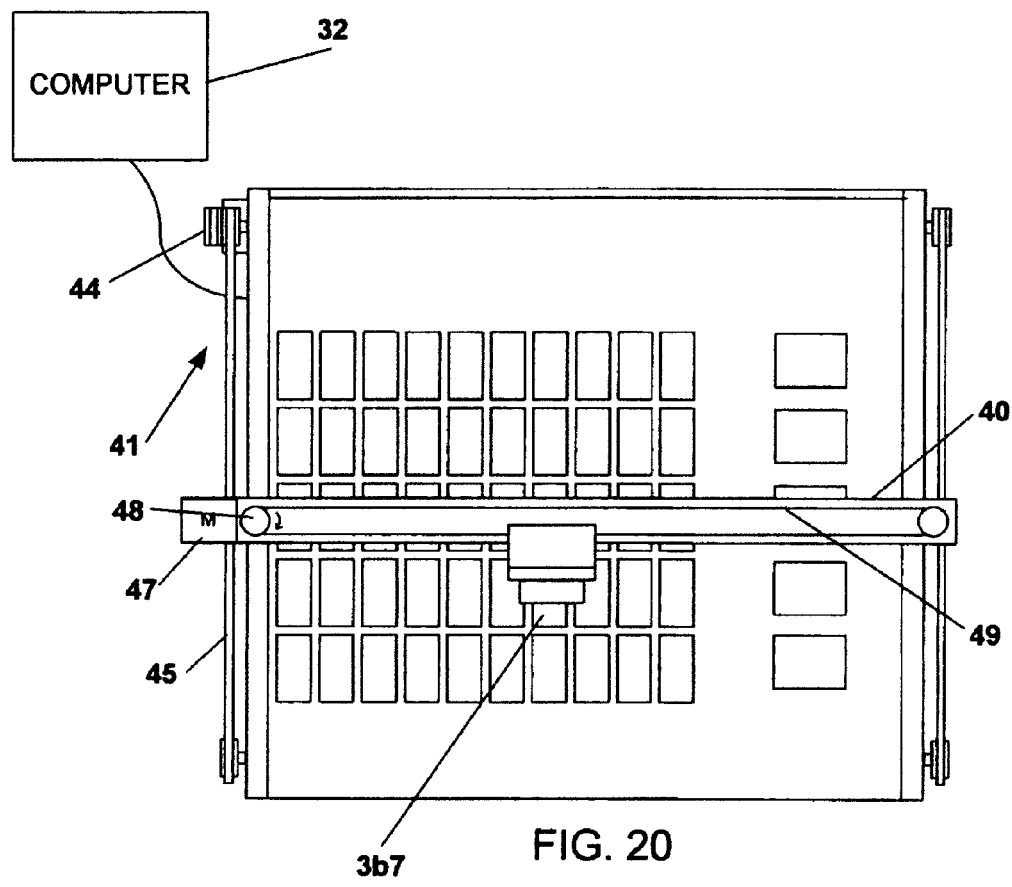
Figure 21:
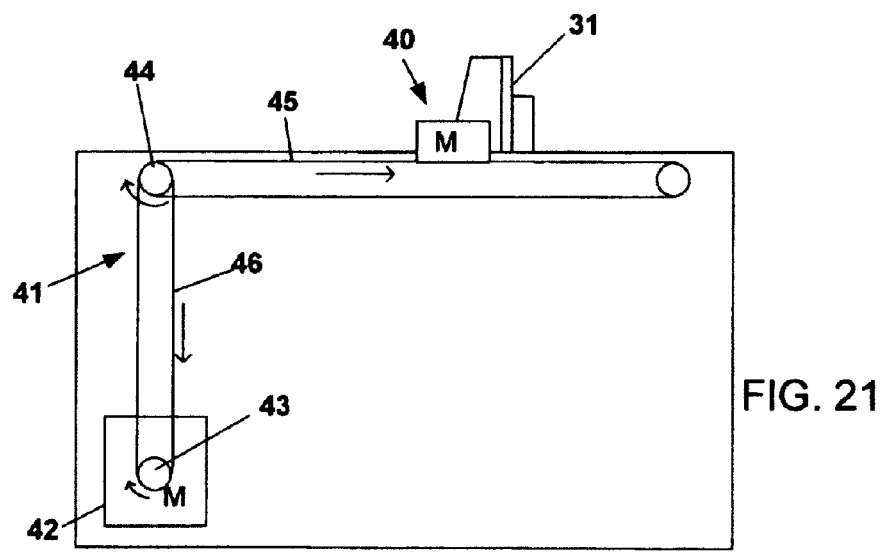

In FIGS. 20 and 21, linear actuators 40 and 41 have been controlled by computer 32 to position robotic syringe grabber 31 over dispenser 3b7. Linear actuators 40 and 41 are preferably belt-driven linear actuators. Motor 42 has turned wheel 43 clockwise. The clockwise motion of wheel 43 has caused belt 46, wheel 44 and belt 45 to also turn clockwise. The clockwise motion of belt 45 has caused linear actuator 40 to move to the right (FIG. 21) so that linear actuator 40 is just above the row of dispensers having dispenser 3b7 (FIG. 20). Concurrently, motor 47 of linear actuator 40 has turned wheel 48 clockwise causing belt 49 to turn clockwise. The clockwise motion of belt 49 has caused robotic syringe grabber 31 to move to the left (FIG. 20) so that it is positioned above dispenser 3b7.

Figure 22:
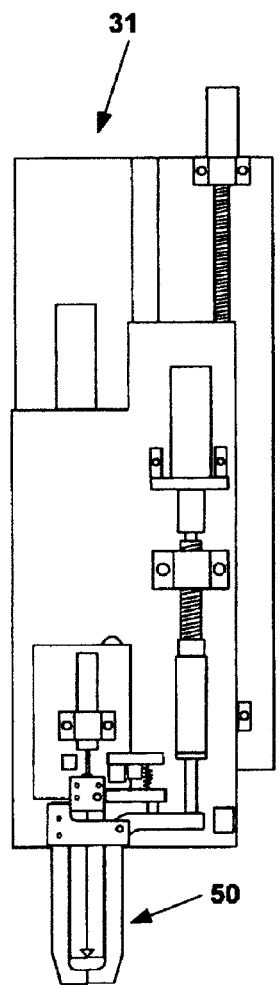

FIG. 22 shows a front view of robotic syringe grabber 31 positioned over dispenser 3b7. Gripper 50 is positioned slightly to the left of the vertical center of dispenser 3b7.

Figure 23:
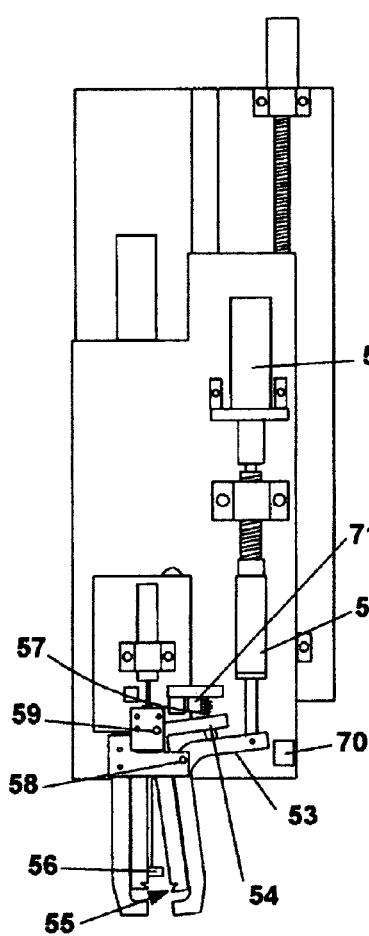

In FIG. 23 motor 51 has controlled linkage 52 so that it has pulled upward on syringe gripper arm 53 of syringe gripper 50 causing syringe gripper arm 53 to turn counterclockwise about axis 58. The counterclockwise motion of syringe gripper arm 53 has pushed syringe plunger arm 54 counterclockwise about axis 59 compressing linear spring 57. The counterclockwise rotations of syringe gripper 50 and plunger gripper 55 have exposed plunger foot 56. Sensor 70 verifies that syringe gripper 50 is open and sensor 71 verifies that plunger gripper 55 is open.

Figure 24:
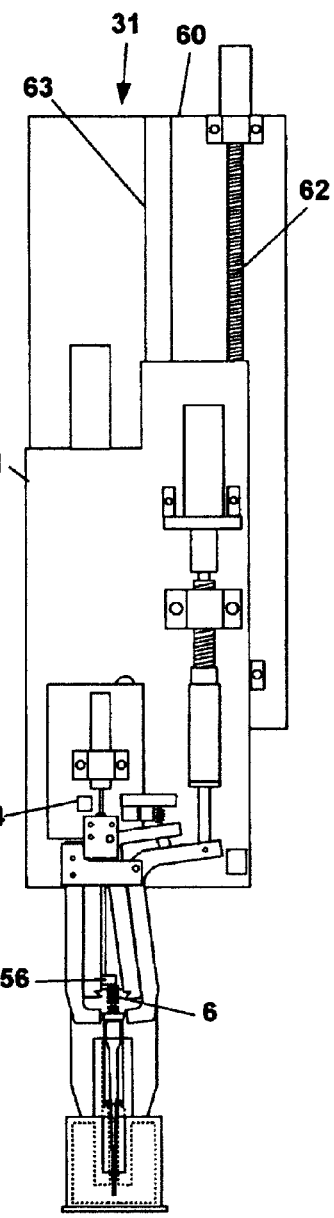

In FIG. 24 a linear actuator motor (not shown) of linear actuator 60 has turned screw 62 of robotic syringe gripper 31 causing platform 61 to move downward on track 63 of linear actuator 60. Platform 61 has moved downward until plunger foot 56 has contacted plunger 6. Plunger present sensor 64 verifies that plunger foot 56 has contacted plunger 6.

Figure 25:
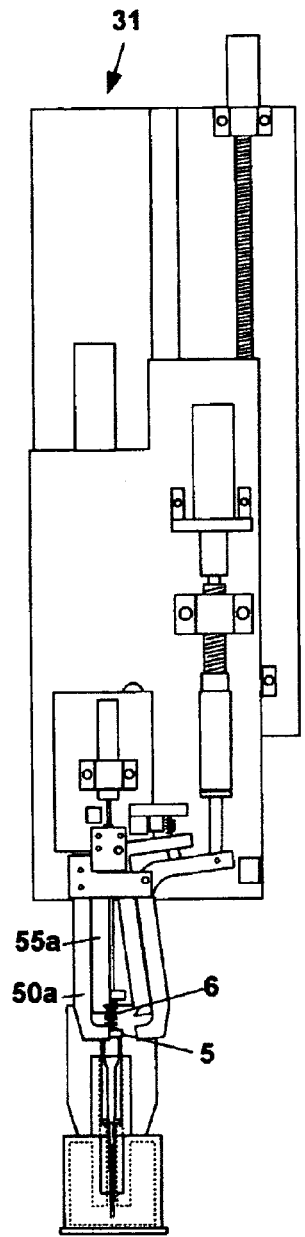

In FIG. 25 computer 32 has moved robotic syringe gripper 31 slightly to the right so that fixed syringe gripper jaw 50a and fixed plunger gripper jaw 55a engage syringe 5 and plunger 6, respectively.

Figure 26:
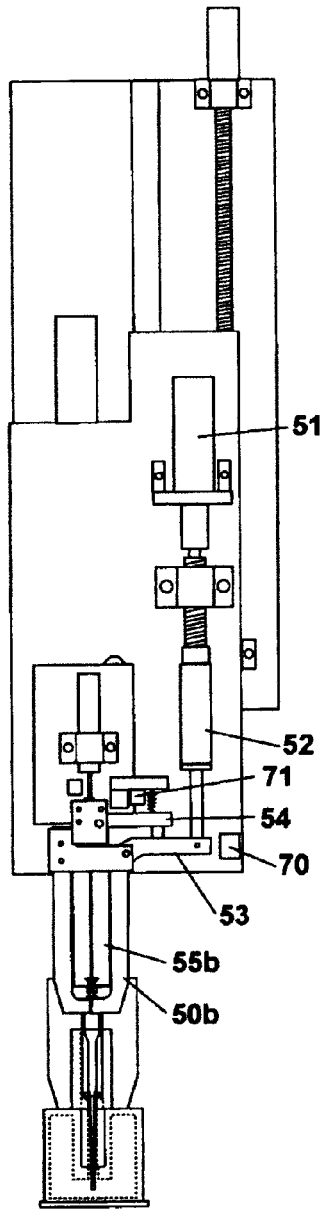

In FIG. 26 motor 51 has controlled linkage 52 so that it has lowered syringe gripper arm 53 of syringe gripper 50 causing syringe gripper arm 53 to turn clockwise. The clockwise motion of syringe gripper arm 53 has allowed linear spring 57 to push syringe plunger arm 54 clockwise. The clockwise rotations of syringe gripper arm 53 and syringe plunger arm 54 have caused syringe gripper jaw 50b and plunger gripper jaw 55b to engage syringe 5 and plunger 6, respectively. Sensor 70 verifies that syringe gripper 50 is closed and not jammed and sensor 71 verifies that plunger gripper 55 is closed and not jammed.

Figure 27:
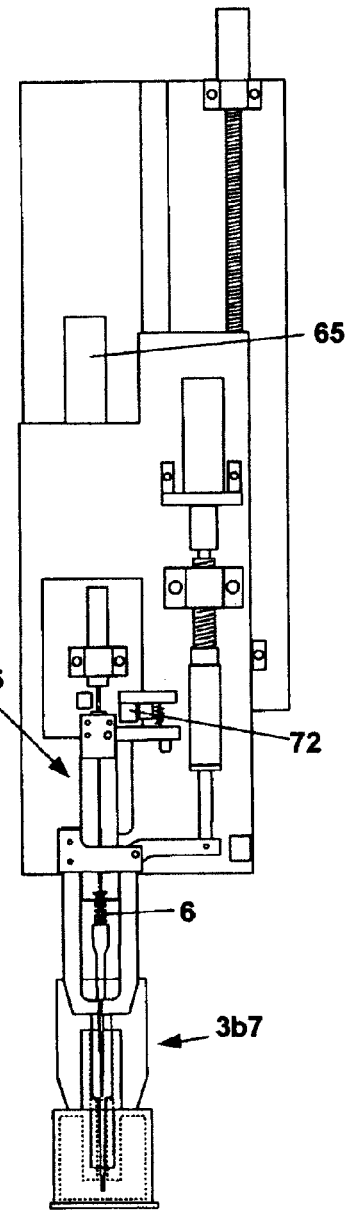
Figure 27B:
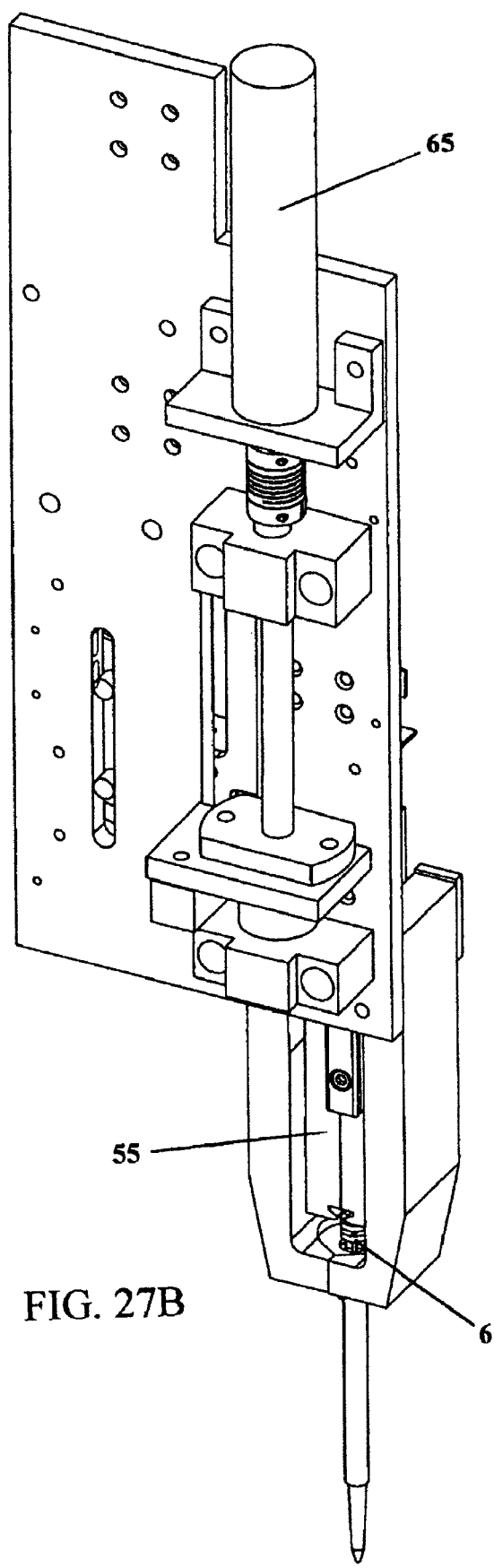

In FIG. 27 plunger motor 65 has raised plunger gripper 55 as shown. A rear perspective view of plunger motor 65 and plunger gripper 55 is shown in FIG. 27B. Plunger gripper 55 is gripping plunger 6. Therefore, plunger 6 has also been raised. The raising of plunger 6 has drawn liquid from dispenser 3b7 (FIG. 27) inside syringe 5 in a fashion similar to that described above in reference to FIG. 9. While liquid is being drawn into syringe 5, the force on plunger 6 is monitored by sensor 72. If the force is outside of acceptable parameters, a warning will be displayed. If the pressure is too low, the plunger may be drawing in air along with the liquid. If the pressure is too high, there may be an obstruction blocking the tip of the plunger.

Figure 28:
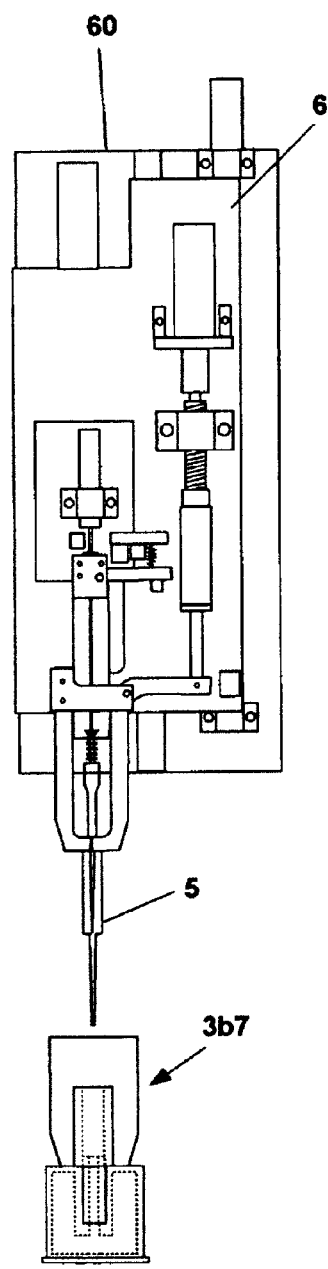

In FIG. 28 linear actuator 60 has raised platform 61 so that syringe 5 is at sufficient height to clear dispenser 3b7.

Figure 29:
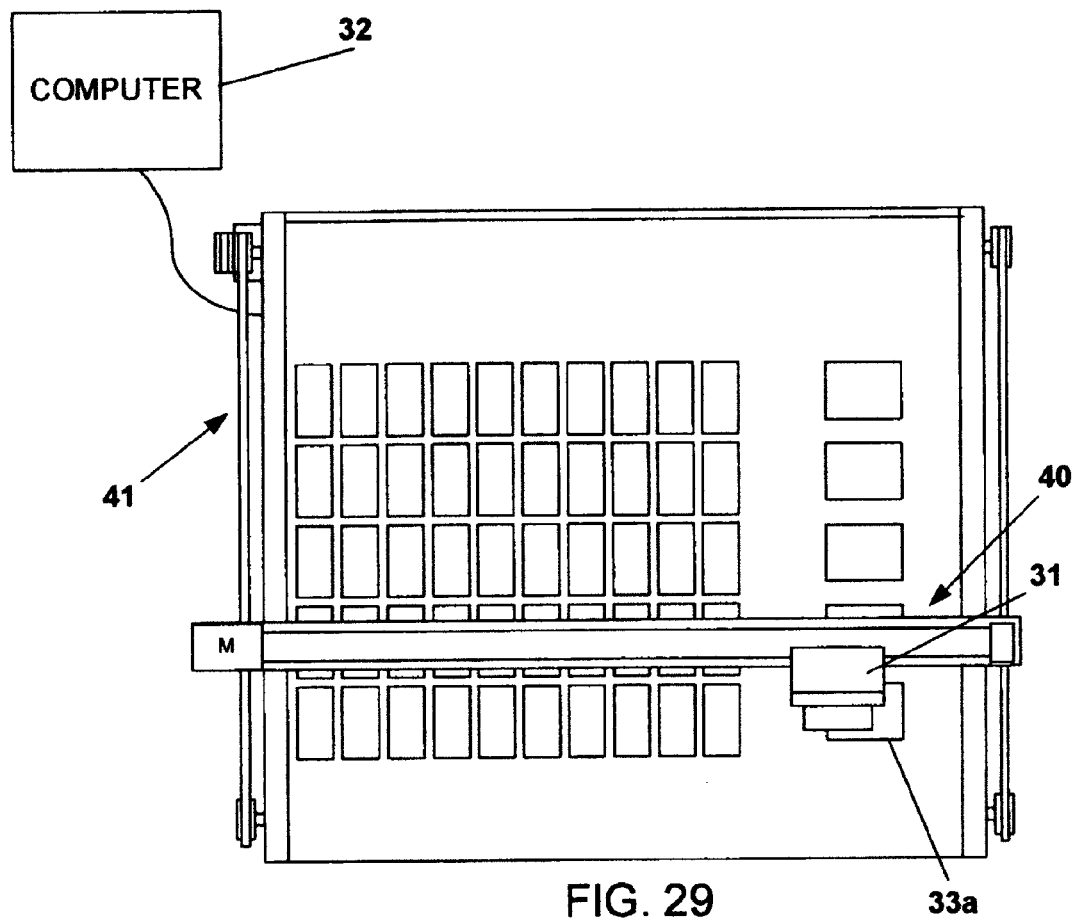
Figure 30:
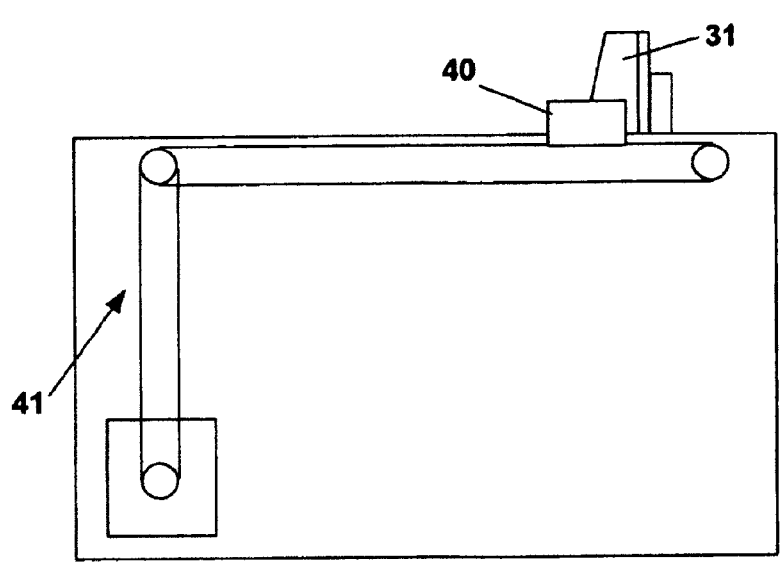

In FIGS. 29 and 30 linear actuators 40 and 41 have been controlled by computer 32 to position robotic syringe grabber 31 over micro-well plate 33a.

Figure 31:
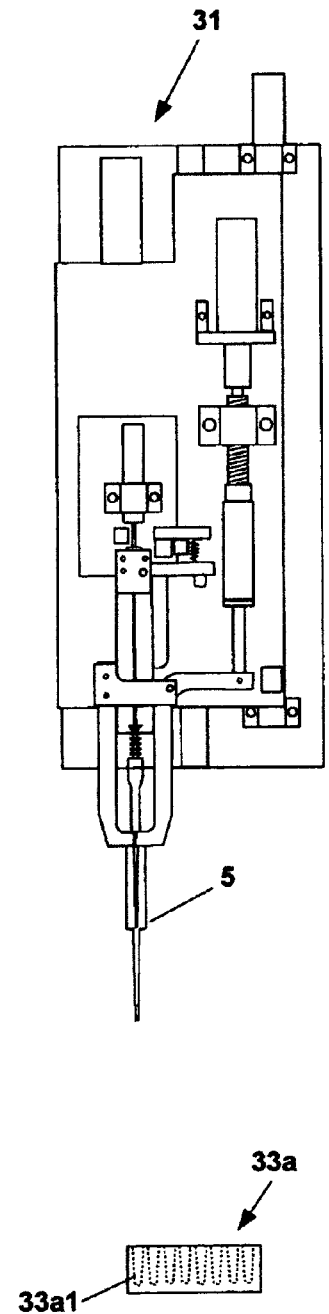

FIG. 31 shows a side view of robotic syringe grabber 31 holding syringe 5 so that it is positioned over well 33a1 of micro-well plate 33a.

Figure 32:
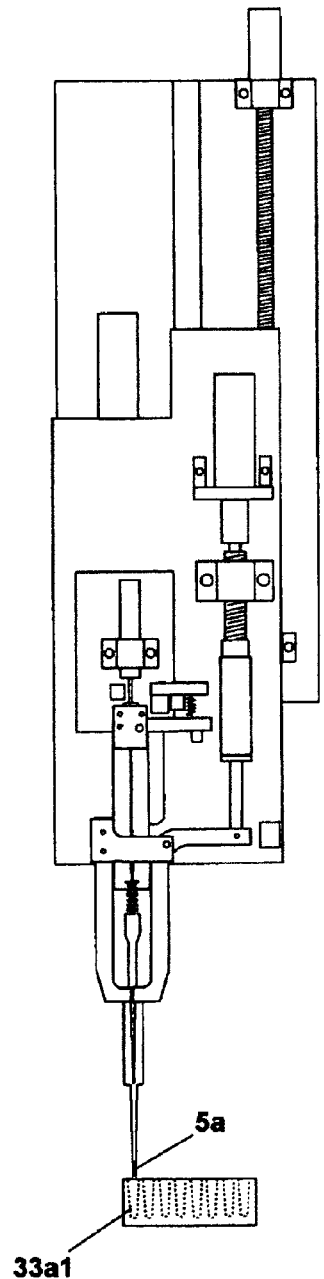

In FIG. 32 linear actuator 60 has lowered platform 61 so that tip 5a of syringe 5 is positioned at a position just above the top of well 33a1.

Figure 33:
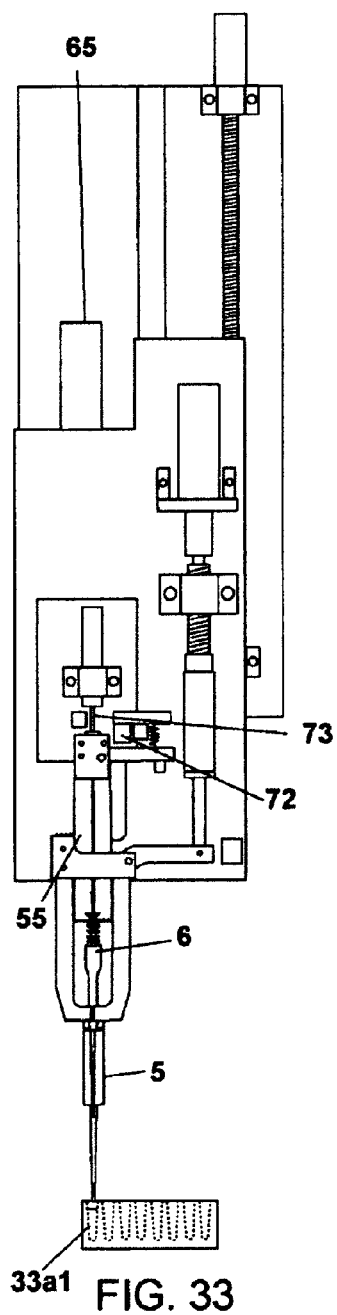

In FIG. 33 plunger motor 65 has lowered plunger gripper 55 causing plunger 6 to be pressed downward. Again, the force on plunger 6 has been monitored by sensor 72. Actuator 73 has been momentarily activated to cause its core rod to bump the top of plunger gripper 55. The repeated bumping has generated shock waves that have been transmitted through plunger gripper 55 to plunger 6 and to syringe 5. The shock waves serve to dislodge any drops that may be adhering to the tip of syringe 5. As shown in FIG. 33, a small amount of liquid has been dispensed into well 33a1.

Figure 34:
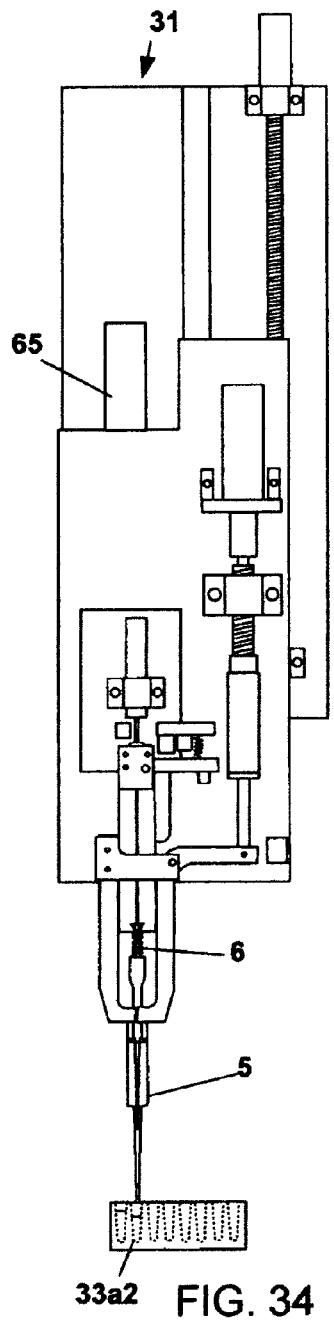

In FIG. 34 linear actuator 40 (FIG. 29) has moved robotic syringe grabber 31 slightly to the right so that syringe 5 is positioned above well 33a2. Plunger motor 65 has further lowered plunger gripper 55 causing plunger 6 to be pressed downward. Actuator 73 has been activated. A small amount of liquid has been dispensed into well 33a2.

Figure 35:
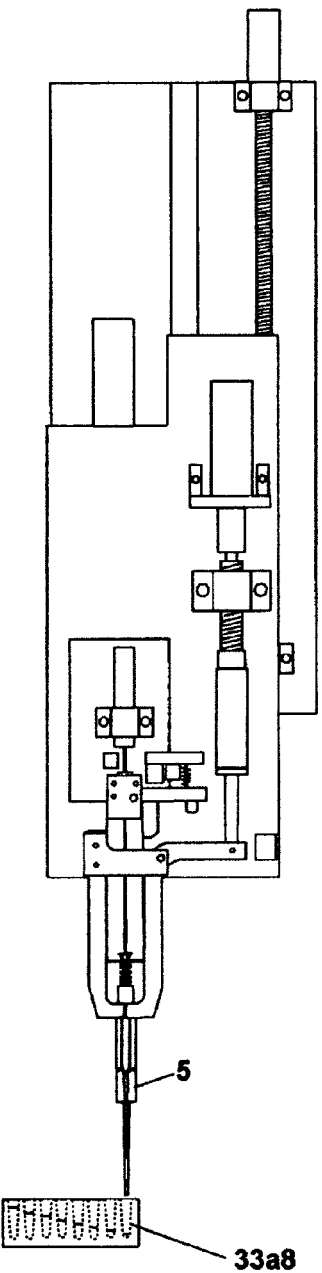

FIG. 35 shows syringe 5 positioned above well 33a8. In a fashion similar to that described in reference to FIGS. 33 and 34, small amounts of liquid have been dispensed in wells 33a3-33a8.

In FIG. 36 linear actuator 60 has raised platform 61.

In FIG. 37, linear actuators 40 and 41 have positioned robotic syringe grabber 31 over dispenser 3b7 (see also FIGS. 20 and 21).

In FIG. 38 linear actuator 60 has lowered platform 61 so that syringe 5 is inside dispenser 3b7.

Figure 39:
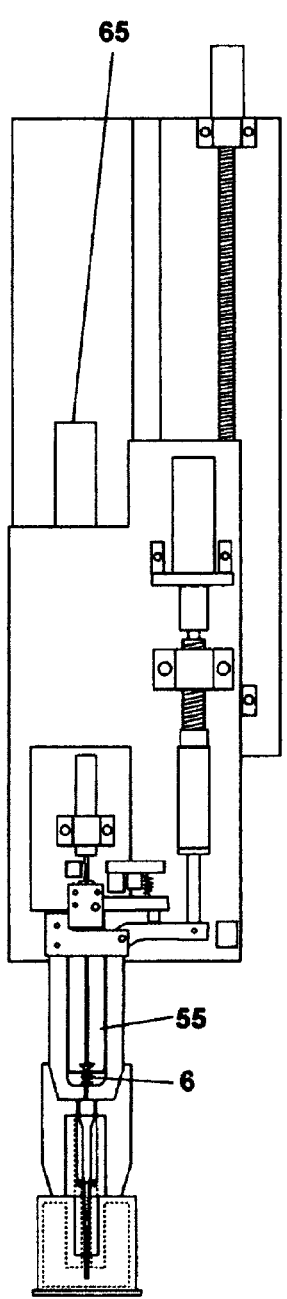

In FIG. 39 plunger motor 65 has lowered plunger gripper 55 causing plunger 6 to be pressed downward. The remaining amount of liquid inside syringe 5 has been returned to dispenser 3b7.

Figure 40:
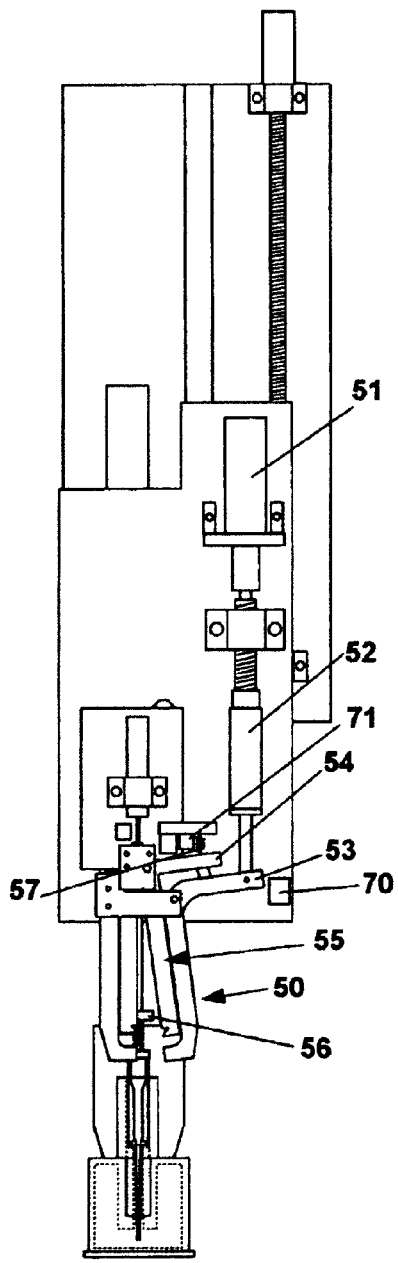

In FIG. 40 motor 51 has controlled linkage 52 so that it has pulled upward on syringe gripper arm 53 of syringe gripper 50 causing syringe gripper arm 53 to turn counterclockwise about axis 58. The counterclockwise motion of syringe gripper arm 53 has pushed syringe plunger arm 54 counterclockwise about axis 59 compressing linear spring 57. The counterclockwise rotations of syringe gripper 50 and plunger gripper 55 have exposed plunger foot 56. Sensor 70 verifies that syringe gripper 50 is open and sensor 71 verifies that plunger gripper 55 is open.

Figure 41:
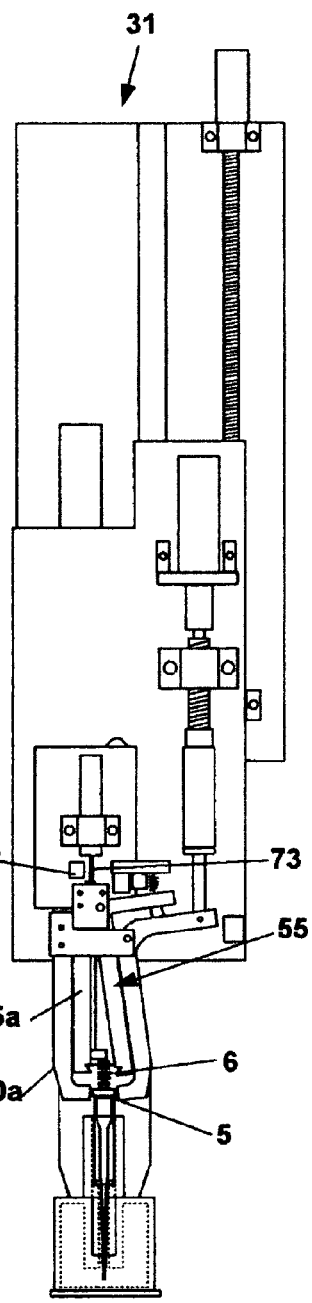

In FIG. 41 linear actuator 40 (FIG. 20) has moved robotic syringe gripper 31 slightly to the left to disengage fixed syringe gripper jaw 50a and fixed plunger gripper jaw 55a from syringe 5 and plunger 6, respectively. Actuator 73 has been activated to bump on the top of plunger gripper 55. The bumping creates shock waves that travel through plunger gripper 55 and syringe gripper 50. The shock waves help ensure that syringe 5 and plunger 6 are totally released from plunger gripper 55 and syringe gripper 50. Plunger present sensor 64 verifies that syringe and plunger have been totally released.

In FIG. 42 linear actuator 60 has raised platform 61. Robotic syringe gripper 31 can now be positioned above another dispenser to remove liquid in a fashion similar to that described above.

For example, in one preferred embodiment robotic syringe gripper 31 is positioned over dispenser 3a1 to remove liquid contained in dispenser 3a1. The solution in dispenser 3a1 is different than the solution in dispenser 3b7. After removing the solution from dispenser 3a1, robotic syringe gripper 31 deposits the solution into wells 33a1-33a8 (FIGS. 33-35) in a fashion similar to that described above. The solutions from dispensers 3a1 and 3b7 are consequently mixed inside the wells of micro-well plate 33a1 to form a chemical solution suitable for use in proteomic crystal trials in protein crystallography.

Locating Indentations

Figure 43:
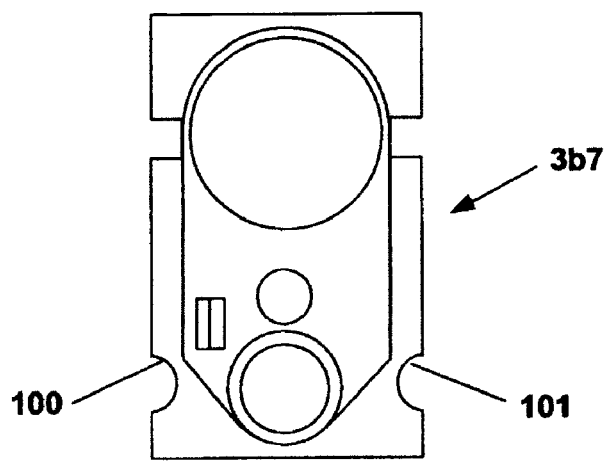
FIGS. 43-44 show the utilization of locating indentations.
Figure 44:
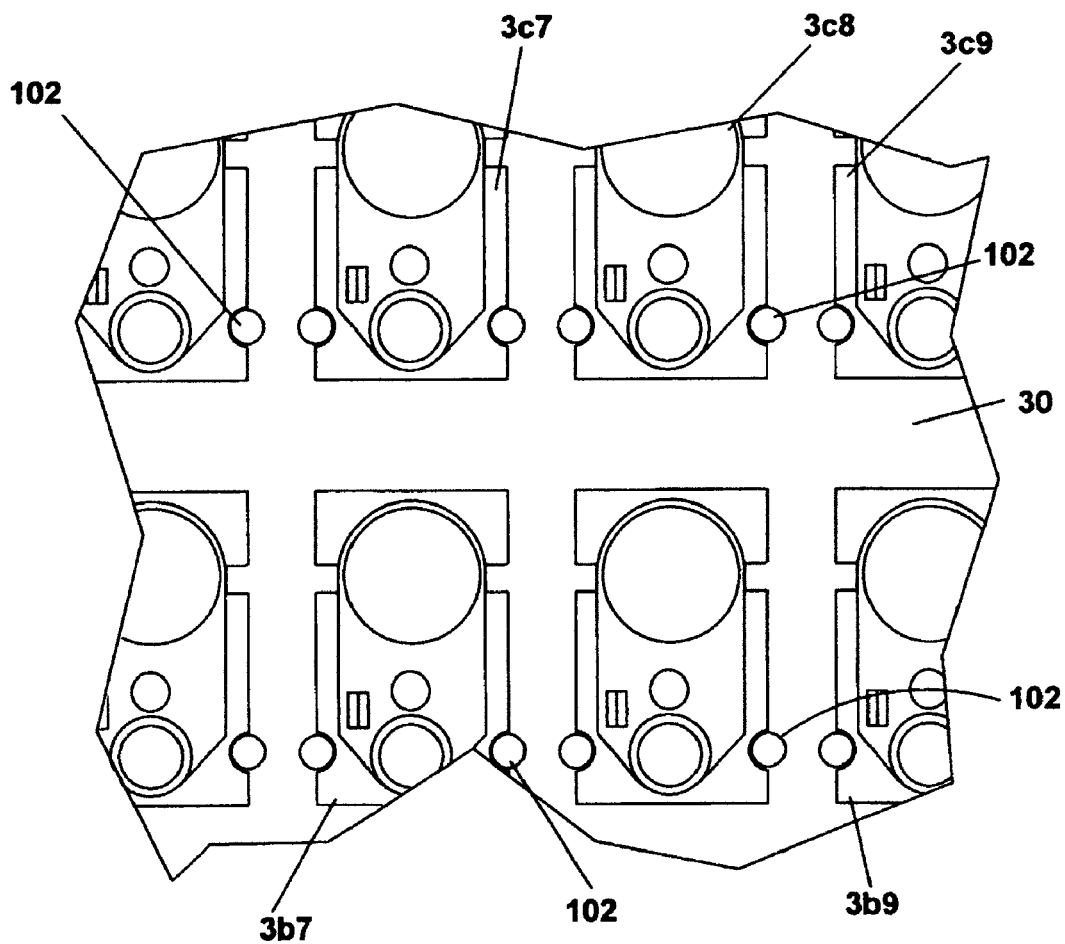

In the third preferred embodiment, dispensers 3a1-3e10 include locating indentations 100 and 101 (FIG. 43). FIG. 43 shows a top view of dispenser 3b7 with locating indentations 101 and 100. FIG. 2A also shows a perspective view of locating indentations 100 and 101. Platform 30 includes locating pins 102 arranged as shown in FIG. 44. Dispensers 3a1-3e10 are arranged on platform 30 so that locating indentations 100 and 101 are aligned with locating pins 102. By utilization of locating pins 102 and locating indentations 100 and 101, dispensers 3a1-3e10 can be precisely positioned on platform 30 and undesirable movement of the dispensers can be virtually eliminated.

Fourth Preferred Embodiment

A fourth preferred embodiment is shown in FIGS. 45-59.

Figure 45:
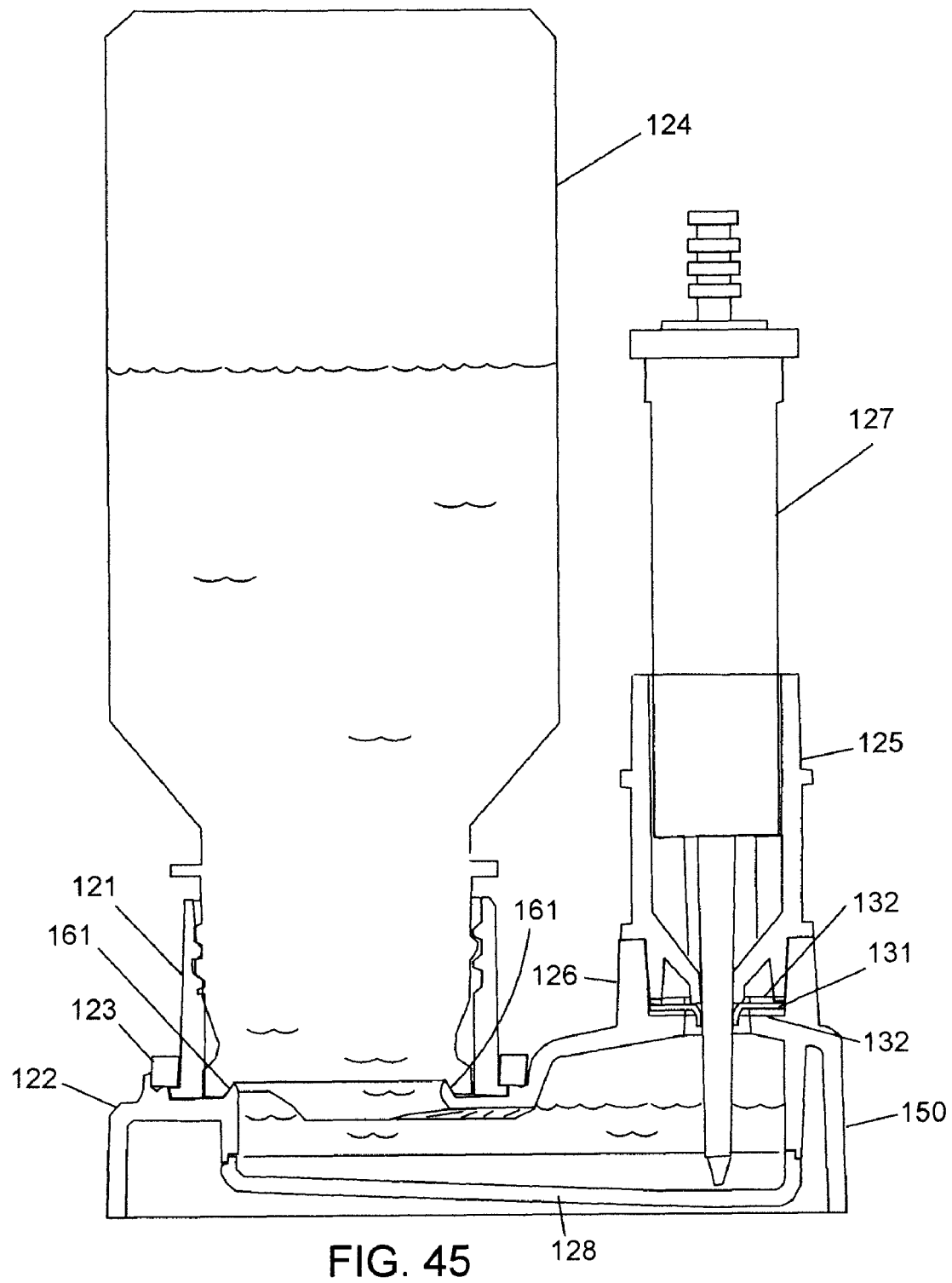
FIG. 45 shows a side view of the fourth preferred embodiment.

In the fourth preferred embodiment, threaded spin ring 121 is attached to upper portion 122 of tray 150 via retaining ring 123 so that threaded spin ring 121 is free to spin (see also FIG. 48). Bottle 124 is threaded onto threaded spin ring 121 (FIG. 45). Syringe adaptor 125 is twist-locked onto the top of adaptor receiver 126. Syringe 127 is inserted into syringe adaptor 126 so that the tip of syringe 127 is just above the top of lower portion 128 of tray 150. Silicon rubber septum 131 is positioned between silicon rubber septum spacers 132. Silicon rubber septum 131 is flexible to allow for passage of syringe 127.

Operation of Fourth Preferred Embodiment

In FIG. 57, syringe 127 has been inserted into syringe adapter of tray 150.

In FIG. 58, a user has grabbed syringe plunger 127b with one hand and has pulled it upward while holding syringe body 127a down with the other hand. The upward movement of syringe plunger 127b has caused liquid from tray 150 to be drawn up inside syringe 127. As liquid is drawn up inside syringe body 127a, the surface level of the liquid inside tray 150 decreases until eventually the level is below the apex of arched roof 160 (see also FIGS. 47, 55, 56). Air is able to enter tray 3 via gaps between syringe 127 and syringe wiper 131 (FIG. 58b). As the surface level decreases below the level of arched roof 160, the vacuum inside bottle 124 will be momentarily broken as air is able to enter bottle 124 and flow upward as air bubbles through the liquid in bottle 124. As the air bubbles are flowing upward, liquid inside bottle 124 is filling tray 150. Liquid will continue to flow out of bottle 124 until once again the level of liquid inside tray 150 is equal to or slightly above the level of the apex of arched roof 160, sealing off the opening and allowing the vacuum inside bottle 124 to reestablish.

In this fashion, liquid can be removed from tray 150 by syringe 127. After liquid has been removed from tray 150 via syringe 127, the user utilizes syringe 127 to deposit the removed liquid into a liquid receptacle device.

Some Features of the Fourth Preferred Embodiment

Air Tight Storage of Fluid

The fourth preferred embodiment allows for air-tight long term storage of fluid. After usage of tray 150, there may still be fluid in the tray. To store the fluid without evaporation, vinyl rubber cap 129 is press fit onto the top of syringe adapter 125 and hard plastic cap 135 is threaded tightly onto the threads of slip ring 121 (FIG. 49). In one preferred embodiment the storage capacity of tray 150 is approximately 10 ml with a 10 ml overflow capacity.

Threaded Spin Ring

The utilization of threaded spin ring 121 (see above) allows for easy attachment of bottle 124. Because a spin ring is used, bottle 124 can be tightened and then aligned properly with tray 150, rather than at an undesirable angle (FIG. 51). Preferably, threaded spin ring 121 has threads that are compatible with common 125 ml and 250 ml NALGENE® laboratory bottles and equivalent lab bottles. NALGENE® is a registered trademark of the Nalge Company Corporation and refers in general to plastic bottles.

Inner Diameter Tapered Bottle Mouth Seal

Figures 46, 46A, 46B:
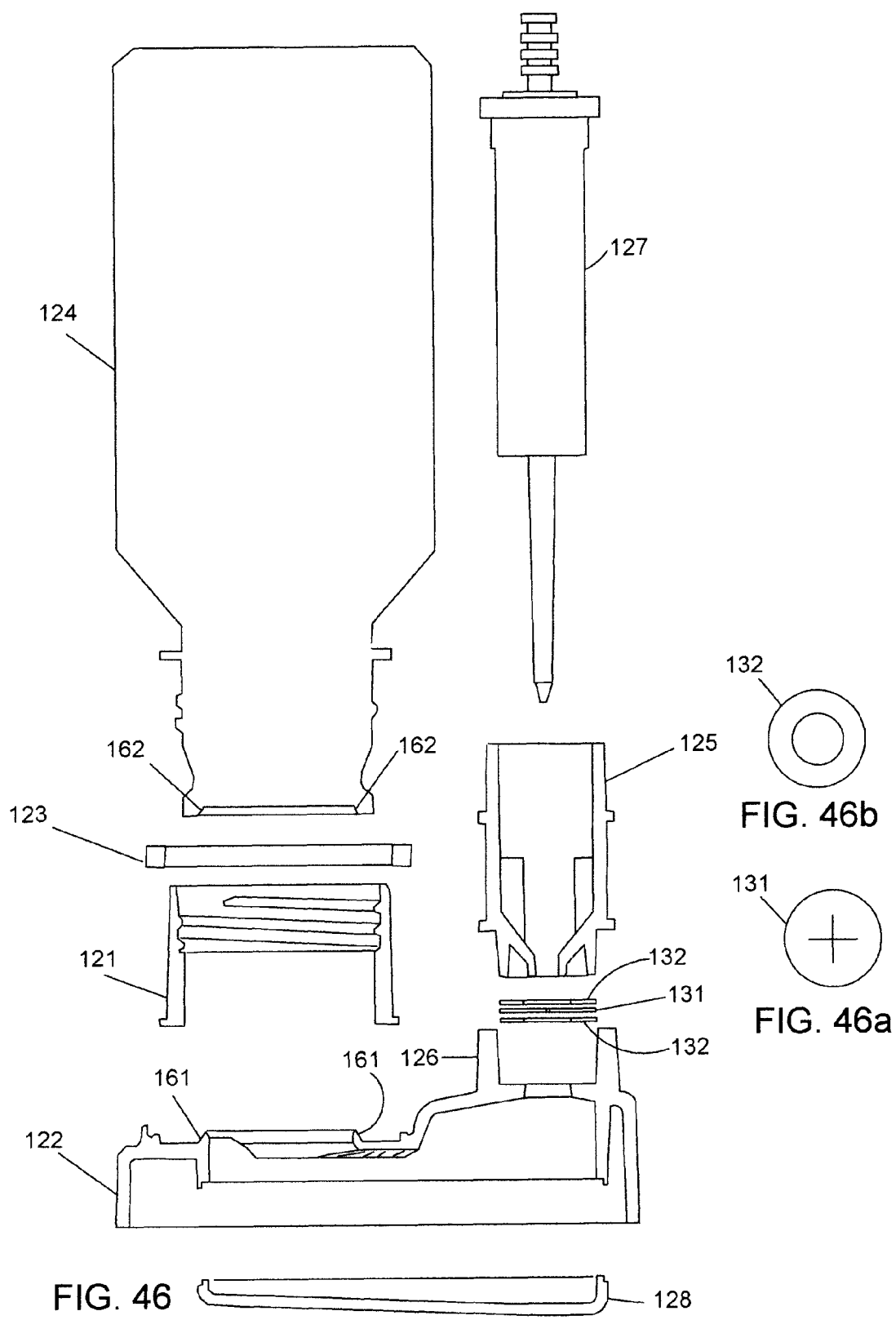
FIG. 46 shows an exploded view of the fourth preferred embodiment.
FIGS. 46a and 46b show syringe wipers and wiper spacers.

Laboratory bottles such as bottle 124 typically have inner diameter 162 at the opening that is tapered as shown in FIG. 46. To mesh best with inner diameter 162, the fourth preferred embodiment includes tapered edges 161. FIG. 45 shows tapered edges 161 meshed with the inner diameter of bottle 124. Tapered inner diameter 162 allows for a tighter seal and enhances fluid flow for high viscosity fluids.

Locking Syringe Adapters

FIG. 45 shows syringe adapter 125. Syringe adapter 125 is configured so that it will position 10 ml syringe 127 so that the tip of syringe 127 is positioned just above the top of lower portion 128 of tray 150. Also, syringe adapter 125 (FIG. 52) includes nodule 154 that slips into slot 155 of adapter receiver 126. To lock syringe adapter 125 down onto adapter receiver 126 the user turns adapter receiver ⅛ turn clockwise after slipping nodule 154 into slot 155 of adapter receiver 126.

Interchangeable Syringe Adapters

Figure 52:
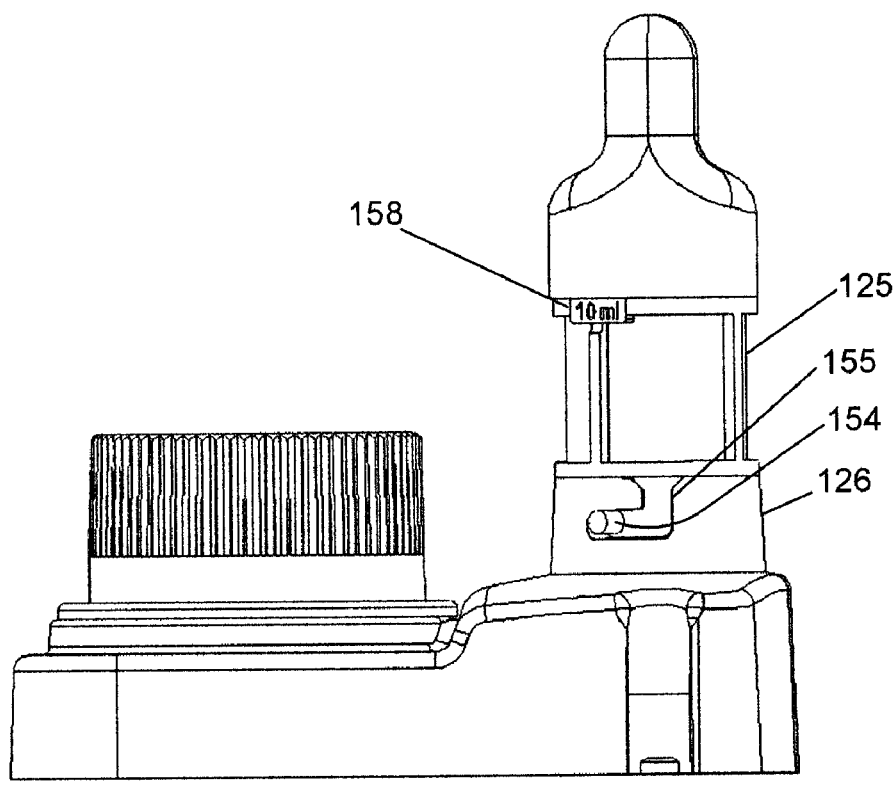
FIG. 52 shows a side view of components of the fourth preferred embodiment.
Figure 53:
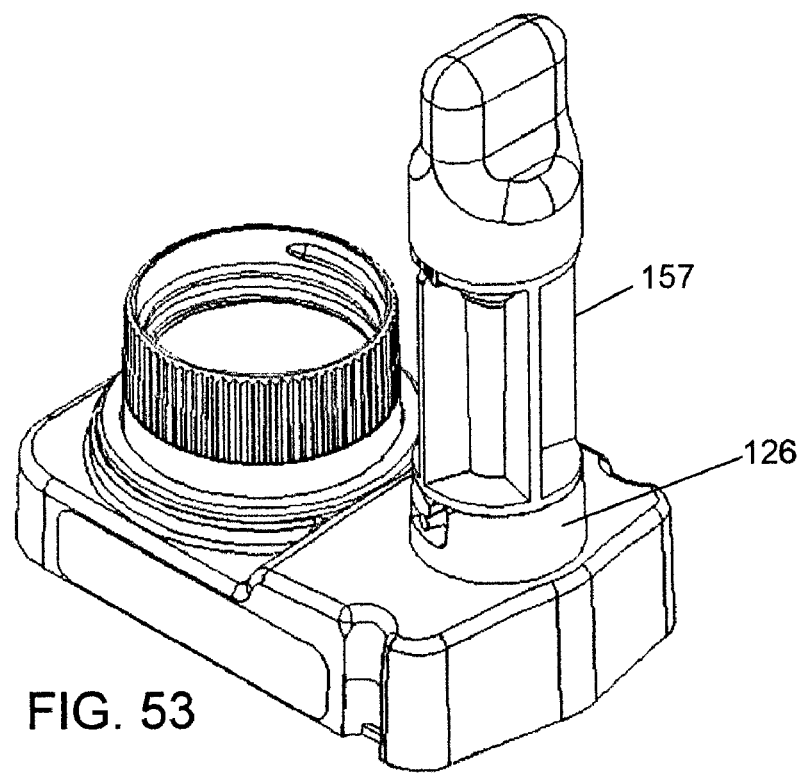
FIG. 53 shows another perspective view of components of the fourth preferred embodiment.

In the fourth preferred embodiment, the syringe adapters are interchangeable so that different sized syringes can be utilized. For example, FIG. 52 shows syringe adapter 125 to accommodate a 10 ml syringe. FIG. 53 shows syringe adapter 157 to accommodate a 1 ml syringe. Likewise, other different sized syringe adapters can be used to accommodate a variety of syringe sizes.

Engraved Syringe Adapter Size Labels

As shown in FIG. 52, in the preferred embodiment the syringe adapters are engraved so that the user can easily determine the appropriate syringe size for the adapter. For example, FIG. 52 shows 10 ml syringe adapter 125 engraved with engraving 158.

Top Installable Syringe Adapter Seal/Syringe Wiper

Silicon rubber syringe wiper 131 and syringe seals 132 are installed by the user prior to attaching the syringe adapter (FIG. 45). Syringe wiper 131 functions to wipe off excess fluid that might adhere to the outside of syringe 127. It should be noted that although FIG. 45 shows one syringe wiper 131, more can be added to increase the wiping effect.

Conically Tapered Inner Tray Bottom

In the preferred embodiment, all points on the surface of lower portion 128 of tray 150 (FIG. 45) taper so that fluid will flow to a point directly below the syringe location (see also FIG. 54). This allows for more efficient removal of the fluid via the syringe.

Tray with Arched Roof

Figure 47:
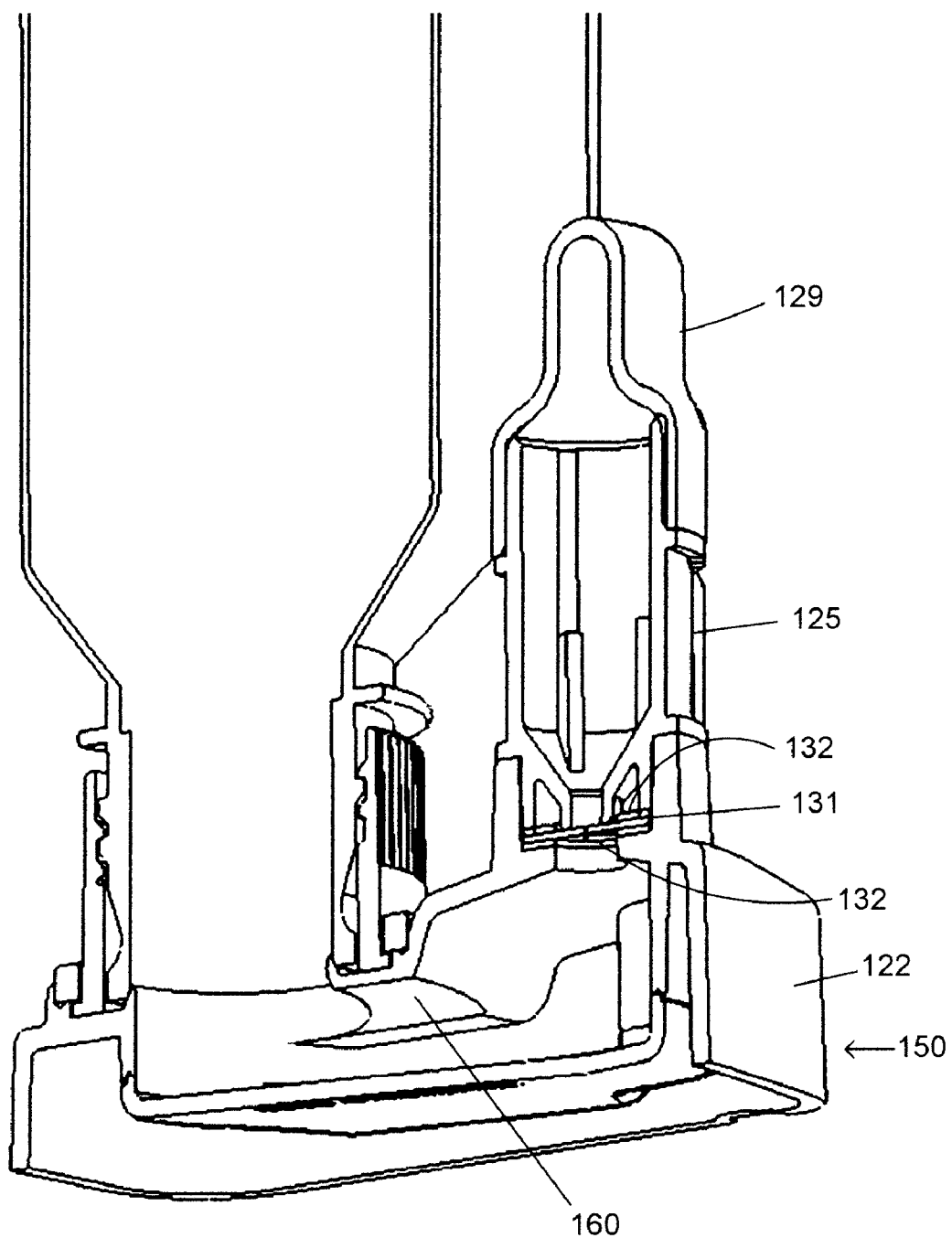
FIG. 47 shows a perspective cut-out view of the fourth preferred embodiment.

In the preferred embodiment, upper portion 122 of tray 150 includes arched roof 160 (FIG. 47). Arched roof 160 allows for efficient bubble formation and flow of bubbles for high viscosity fluids (FIG. 55). Due to surface tension, bubbles have an easier time forming and flowing when the roof section 160 is arched. For example, as the surface level of the fluid below the syringe decreases below the level of arched roof 160, the vacuum inside bottle 124 will be momentarily broken as air is able to enter bottle 124 and flow upward as air bubbles through the liquid in bottle 124. As the air bubbles are flowing upward, liquid inside bottle 124 is filling tray 150. Liquid will continue to flow out of bottle 124 until once again the level of liquid inside tray 150 is equal to or slightly above the level of the top of the arch of arch 160, sealing off arch 160 and allowing the vacuum inside bottle 124 to reestablish (FIG. 56).

Conically Shaped Inner Tray Top

In a manner similar to the conically shaped lower portion 128 of tray 150, the inner top of upper portion 122 is also conically shaped to allow for optimum fluid flow when tray 150 is turned upside down. For example, FIG. 59 shows an inverted upper portion 122 of tray 150. The conical shape allows for optimum fluid flow when draining fluid back into bottle 124 or when after having placed tray 150 on a drying rack after washing the tray during a cleaning process.

Color Coded Barcode Label

The fourth preferred embodiment includes color coded barcode label 171 (FIG. 49). The user can read the words on barcode label 171 and see that it says to use a "White Syringe Adapter/10 ml size". The user then can locate white 10 ml adapter 125 and attach it as described above. An automated machine that utilizes a barcode reader can then use the barcode reader to read the barcode on barcode label 171. The automated machine is programmed to lower its syringe to an appropriate level to match the height of syringe adapter 125. In a preferred embodiment a white label is utilized in conjunction with a 10 ml syringe adapter, a blue label is utilized in conjunction with a 1.0 ml syringe adapter, and a red label is utilized in conjunction with a 0.1 ml syringe adapter. Likewise, other different colored labels can be utilized to match a variety of different syringe adapter sizes.

Although the above-preferred embodiments have been described with specificity, persons skilled in this art will recognize that many changes to the specific embodiments disclosed above could be made without departing from the spirit of the invention. For example, bottle 1 (FIG. 2B) can be made out of other materials besides plastic. In one preferred embodiment, for example, bottle 1 is glass. Also, retaining clip 4 can be made out of variety of materials such as plastic or metal. Also, tilted bottom component 9 can be molded such that its vertical sides extend up inside dispenser 3 to a height that is higher than the dispensing level. This would help minimize that possibility of liquid leaking through the connection of bottom component 9. Also, although it was described in detail how robotic syringe grabber 31 (FIG. 17) is utilized to remove syringes from dispensers 3a1-3e10, it should be recognized that robotic syringe grabber 31 can also be utilized to similarly remove syringes from a variety of dispenser types for the purpose of dispensing liquid. For example, robotic syringe grabber 31 can be used to remove a syringe from a simple bottle having a syringe positioned at its opening. Therefore, the attached claims and their legal equivalents should determine the scope of the invention.

What is claimed is:

1. A liquid dispensing device, comprising:
A. a tray for holding a liquid at a relatively constant level defining an approximately constant tray liquid level, B. a liquid container containing a liquid having an opening and positioned upside-down in said tray such that atmospheric pressure on the liquid in said tray and vacuum inside said container prevents liquid from draining from said container except when the liquid level in said tray drops to a level sufficient to allow air into said liquid container and to allow fluid to flow from said liquid container into said tray so that the level of the liquid in said tray returns to said approximately constant tray liquid level, and C. a syringe for drawing liquid from said tray, wherein positioning of said syringe for drawing fluid is simplified by reason of the fact that the level of fluid in said tray is maintained at said approximately constant level despite withdrawal of quantities of fluid from said tray.

2. The liquid dispensing device as in claim 1, wherein said tray is air-tight to allow for long term air-tight storage of fluid.

3. The liquid dispensing device as in claim 1, wherein said tray further comprises a threaded spin ring for attaching said liquid container to said tray.

4. The liquid dispensing device as in claim 3, wherein said liquid dispensing device is at least one liquid dispensing device, wherein said automated liquid handling device comprises:

A. a robotic syringe grabber positionable above said at least one liquid dispensing device, B. at least one horizontal positioning linear actuator for horizontally positioning said robotic syringe grabber above said at least one liquid dispensing device, and C. a computer programmed to control said at least one horizontal positioning linear actuator and said robotic syringe grabber.

5. The liquid dispensing device as in claim 1, wherein said tray comprises a tapered opening to mesh with tapered diameter of said liquid container for an air-tight seal.

6. The liquid dispensing device as in claim 1, further comprising a locking syringe adapter for receiving said syringe.

7. The liquid dispensing device as in claim 1 wherein said syringe is a plurality of differently sized syringes, further comprising a plurality of interchangeable syringe adapters, each interchangeable syringe adapter configured to receive one of said plurality of differently sized syringes.

8. The liquid dispensing device as in claim 1, further comprising a syringe adapter for receiving said syringe, wherein said syringe adapter is engraved with the size of said syringe.

9. The liquid dispensing device as in claim 1, further comprising at least one syringe wiper for wiping off excess fluid on said syringe.

10. The liquid dispensing device as in claim 1, wherein said tray comprises a conically tapered inner tray bottom.

11. The liquid dispensing device as in claim 1, wherein said tray comprises a conically tapered inner tray top.

12. The liquid dispensing device as in claim 1, wherein said tray comprises:

A. a liquid container receiving section for receiving said liquid container, and B. a syringe receiving section for receiving said syringe, C. an arched roof section between said liquid container receiving section and said syringe receiving section, wherein air flows from said syringe receiving section to said liquid container receiving section via said arched roof section and fluid flows from said liquid container receiving section to said syringe receiving section via said arched roof section.

13. The liquid dispensing device as in claim 1, wherein said syringe is manually removably inserted into said liquid dispensing device by the hand of an operator.

14. The liquid dispensing device as in claim 1, wherein said syringe is automatically removably inserted into said liquid dispensing device by the utilization of an automated machine, and wherein liquid is automatically transferred to a liquid receiving device.

15. The liquid dispensing device as in claim 14, wherein said automated machine comprises a barcode reader and said tray comprises a tray barcode, wherein said tray barcode comprises information indicative of the size of a syringe adapter attached to said tray.

16. The liquid dispensing device as in claim 15, wherein said tray barcode and said syringe adapter are color coded to match.

17. The liquid dispensing device as in claim 14, wherein said syringe means is manually removably inserted into said liquid dispensing device by the hand of an operator.

18. The liquid dispensing device as in claim 14, wherein said syringe means is automatically removably inserted into said liquid dispensing device by the utilization of an automated liquid mixing means, and wherein liquid is automatically transferred to a liquid receiving means.

19. A liquid dispensing device, comprising:

A. a tray means for holding a liquid at a relatively constant level defining an approximately constant tray liquid level, B. a liquid container means containing a liquid having an opening and positioned upside-down in said tray such that atmospheric pressure on the liquid in said tray means and vacuum inside said container means prevents liquid from draining from said container means except when the liquid level in said tray means drops to a level sufficient to allow air into said liquid container means and to allow fluid to flow from said liquid container means into said tray means so that the level of the liquid in said tray means returns to said approximately constant tray liquid level, and C. a syringe means for drawing fluid from said tray means, wherein positioning of said syringe means for drawing fluid is simplified by reason of the fact that the level of fluid in said tray means is maintained at an approximately constant level despite withdrawal of quantities of fluid from said tray means.

20. A method for dispensing liquid, comprising the steps of:

A. inserting a syringe into a liquid dispensing device, wherein said liquid dispensing device comprises:

1. a tray for holding a liquid at a relatively constant level defining an approximately constant tray liquid level, and 2. a liquid container containing a liquid having an opening and positioned upside-down in said tray such that atmospheric pressure on the liquid in said tray and vacuum inside said container prevents liquid from draining from said container except when the liquid level in said tray drops to a level sufficient to allow air into said liquid container and to allow fluid to flow from said liquid container into said tray so that the level of the liquid in said tray returns to said approximately constant tray liquid level, wherein positioning of said syringe for drawing fluid is simplified by reason of the fact that the level of fluid in said tray is maintained at an approximately constant level despite withdrawal of quantities of fluid from said tray, B. drawing liquid into said syringe, C. removing said syringe from said liquid dispensing device, and D. dispensing liquid from said syringe into a liquid receiving device.

21. A liquid dispensing device, comprising:

A. a tray for holding a liquid,

B. a liquid container containing a liquid having an opening and positioned upside-down in said tray such that liquid from said container maintains a liquid level in said tray at an approximately constant liquid level such that atmospheric pressure on the liquid in said tray and the vacuum inside said container prevents liquid from draining from said container except when the liquid level in said tray drops to a level sufficient to permit a small quantity of liquid to drain from said container and to permit a small quantity of air to enter said container, and C. a syringe for drawing fluid from said tray, wherein positioning of said syringe for drawing fluid is simplified by reason of the fact that the level of liquid in said tray is maintained at an approximately constant level despite withdrawal of quantities of liquid from said tray.

* * * * *

UNITED STATES PATENT AND TRADEMARK OFFICE
Certificate

Patent No. 7,815,865 B2                                                                               Patented: October 19, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: John Hoffman, Poway, CA (US); James A. Benjamin, San Diego, CA (US); Janet M. Newman, Melbourne (AU); John Andrew Moulds, Encinitas, CA (US); David W. Jewell, San Diego, CA (US); John A. Adams, Escondido, CA (US); Thomas E. Vomdran, Oceanside, CA (US); Brian L. Ganz, Carlsbad, CA (US); and Michael C. Willis, La Jolla, CA (US).

Signed and Sealed this Thirtieth Day of August 2011.

EDWARD J. GLICK
*Supervisory Patent Examiner*
Art Unit 2882
Technology Center 2800